US011096607B2

(12) United States Patent
Carroll et al.

(10) Patent No.: US 11,096,607 B2
(45) Date of Patent: Aug. 24, 2021

(54) SYSTEMS AND METHODS FOR THERMOREGULATORY SWEAT TESTING

(71) Applicant: ANN AND ROBERT H. LURIE CHILDREN'S HOSPITAL OF CHICAGO, Chicago, IL (US)

(72) Inventors: Michael S. Carroll, Chicago, IL (US); Debra E. Weese-Mayer, Chicago, IL (US)

(73) Assignee: ANN AND ROBERT H. LURIE CHILDREN'S HOSPITAL OF CHICAGO, Chicago, IL (US)

(*) Notice: Subject to any disclaimer, the term of this patent is extended or adjusted under 35 U.S.C. 154(b) by 76 days.

(21) Appl. No.: 16/431,200

(22) Filed: Jun. 4, 2019

(65) Prior Publication Data
US 2019/0365299 A1 Dec. 5, 2019

Related U.S. Application Data

(60) Provisional application No. 62/680,099, filed on Jun. 4, 2018.

(51) Int. Cl.
*A61B 5/145* (2006.01)
*A61B 5/00* (2006.01)
*A61B 5/01* (2006.01)

(52) U.S. Cl.
CPC ........ *A61B 5/14521* (2013.01); *A61B 5/0077* (2013.01); *A61B 5/4266* (2013.01); *A61B 5/0064* (2013.01); *A61B 5/01* (2013.01)

(58) Field of Classification Search
CPC . A61B 5/14521; A61B 5/0077; A61B 5/4266; A61B 5/0064; A61B 5/01
USPC .......................................................... 382/128
See application file for complete search history.

(56) References Cited

U.S. PATENT DOCUMENTS

2008/0275310 A1* 11/2008 Kim ................... A61B 5/4266
600/300
2014/0364777 A1* 12/2014 Swyer ................. A61H 9/0057
601/11

OTHER PUBLICATIONS

Barnes RB. Diagnostic thermography. Appl Opt 7: 1673-1685, 1968.
(Continued)

*Primary Examiner* — Wednel Cadeau
(74) *Attorney, Agent, or Firm* — Locke Lord LLP; Tim Tingkang Xia, Esq.

(57) ABSTRACT

A system for thermoregulatory sweat testing of a subject includes a chamber for accommodating the subject, the chamber having a heating device for operably elevating the core body temperature of the subject to a target temperature so as to induce sweating over a skin surface of the subject; a cooling device for operably creating forced evaporative cooling of the skin surface of the subject after the core body temperature of the subject is elevated to the target temperature; an imaging device for acquiring images of the subject at different times, each image having imaged pixels, the imaging device including one or more infrared cameras, one or more infrared sensors, or a combination of them; and a controller coupled with the chamber and the imaging device for controlling operations of the chamber and the imaging device and processing the acquired images to determine skin surface sweat distributions of the subject.

19 Claims, 15 Drawing Sheets
(12 of 15 Drawing Sheet(s) Filed in Color)

(56) References Cited

OTHER PUBLICATIONS

Birklein F, Riedl B, Claus D, and Neundorfer B. Pattern of autonomic dysfunction in time course of complex regional pain syndrome. Clin Auton Res 8: 79-85, 1998.

Birklein F, Sittl R, Spitzer A, Claus D, Neundorfer B, and Handwerker HO. Sudomotor function in sympathetic reflex dystrophy. Pain 69: 49-54, 1997.

Bouzida N, Bendada A, and Maldague XP. Visualization of body thermoregulation by infrared imaging. Journal of Thermal Biology 34: 120-126, 2009.

Brelsford KL, and Uematsu S. Thermographic presentation of cutaneous sensory and vasomotor activity in the injured peripheral nerve. J Neurosurg 62: 711-715, 1985.

Bucher F, Schneider C, Blau T, Cursiefen C, Fink GR, Lehmann HC, and Heindl LM. Small-Fiber Neuropathy Is Associated With Corneal Nerve and Dendritic Cell Alterations: An In Vivo Confocal Microscopy Study. Cornea 34: 1114-1119, 2015.

Clark RP. Human Skin Temperature and Its Relevance in Physiology and Clinical Assessment. In: Recent Advances in Medical Thermology, edited by Ring EFJ, and Phillips B. Boston, MA: Springer New York, 1984, p. 5-15.

Clark RP, Mullan BJ, and Pugh LG. Skin temperature during running—a study using infra-red colour thermography. J Physiol 267: 53-62, 1977.

Cohen J, Low P, Fealey R, Sheps S, and Jiang NS. Somatic and autonomic function in progressive autonomic failure and multiple system atrophy. Ann Neurol 22: 692-699, 1987.

Davis MD, Genebriera J, Sandroni P, and Fealey RD. Thermoregulatory sweat testing in patients with erythromelalgia. Arch Dermatol 142: 1583-1588, 2006.

Deng ZS, and Liu J. Enhancement of thermal diagnostics on tumors underneath the skin by induced evaporation. Conf Proc IEEE Eng Med Biol Soc 7: 7525-7528, 2005.

Fealey R. Thermoregulatory Sweat Test. In: Clinical Autonomic Disorders: Third Edition. Baltimore, MD: Lippincott Williams & Wilkins, 2008, p. 244-260.

Fealey R. Thermoregulatory Sweat Test. In: Clinical Autonomic Disorders 2nd ed. Philadelphia: Lippincott-Raven, 1997, p. 245-257.

Fushimi H, Inoue T, Nishikawa M, Matsuyama Y, and Kitagawa J. A new index of autonomic neuropathy in diabetes mellitus: heat stimulated thermographic patterns. Diabetes Res Clin Pract 1: 103¬107, 1985.

Guttmann L. The management of the quinizarin sweat test (Q.S.T.). Postgrad Med J 23: 353-366, 1947.

Huygen FJ, Niehof S, Klein J, and Zijlstra FJ. Computer-assisted skin videothermography is a highly sensitive quality tool in the diagnosis and monitoring of complex regional pain syndrome type I. Eur J Appl Physiol 91: 516-524, 2004.

Kuntz NL, Hemenway KL, and Fealey RD. Utility of diagnostic thermoregulatory sweat test in children. In: NeurologyLippincott Williams & Wilkins 530 Walnut St, Philadelphia, PA 19106-3621 USA, 2011, p. A575-A575.

Lahiri BB, Bagavathiappan S, Jayakumar T, and Philip J. Medical applications of infrared thermography: A review. Infrared Physics & Technology 55: 221-235, 2012.

Low PA. Testing the autonomic nervous system. Semin Neurol 23: 407-421, 2003.

Low PA, Caskey PE, Tuck RR, Fealey RD, and Dyck PJ. Quantitative sudomotor axon reflex test in normal and neuropathic subjects. Ann Neurol 14: 573-580, 1983.

Low PA, Tomalia VA, and Park KJ. Autonomic function tests: some clinical applications. Journal of clinical neurology (Seoul, Korea) 9: 1-8, 2013.

Low PA, Walsh JC, Huang CY, and McLeod JG. The sympathetic nervous system in diabetic neuropathy. A clinical and pathological study. Brain 98: 341-356, 1975.

Provitera V, Gibbons CH, Wendelschafer-Crabb G, Donadio V, Vitale DF, Stancanelli A, Caporaso G, Liguori R, Wang N, Santoro L, Kennedy WR, and Nolano M. A multi-center, multinational age- and gender-adjusted normative dataset for immunofluorescent intraepidermal nerve fiber density at the distal leg. Eur J Neurol 23: 333-338, 2016.

Saxena AK, and Willital GH. Infrared thermography: experience from a decade of pediatric imaging. Eur J Pediatr 167: 757-764, 2008.

Shahani BT, Halperin JJ, Boulu P, and Cohen J. Sympathetic skin response—a method of assessing unmyelinated axon dysfunction in peripheral neuropathies. J Neurol Neurosurg Psychiatry 47: 536-542, 1984.

Sun PC, Lin HD, Jao SH, Chan RC, Kao MJ, and Cheng CK. Thermoregulatory sudomotor dysfunction and diabetic neuropathy develop in parallel in at-risk feet. Diabet Med 25:413-418, 2008.

Torii M, Yamasaki M, Sasaki T, and Nakayama H. Fall in skin temperature of exercising man. Br J Sports Med 26: 29-32, 1992.

\* cited by examiner

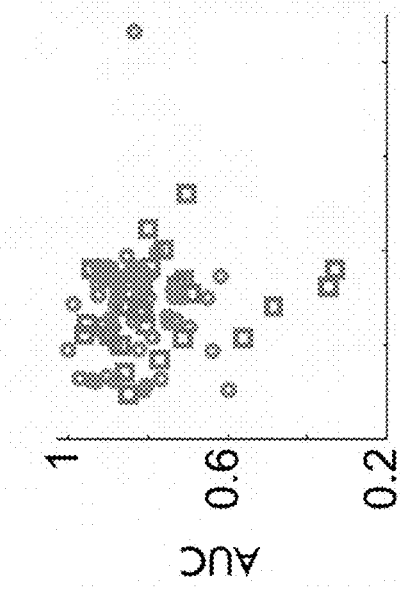
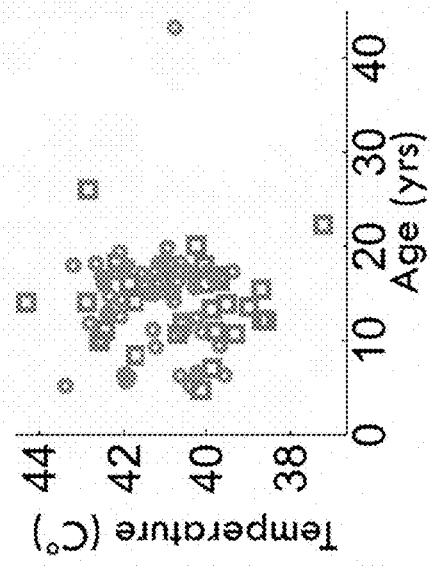
FIG. 5A  FIG. 5B  FIG. 5C  FIG. 5D  FIG. 5E

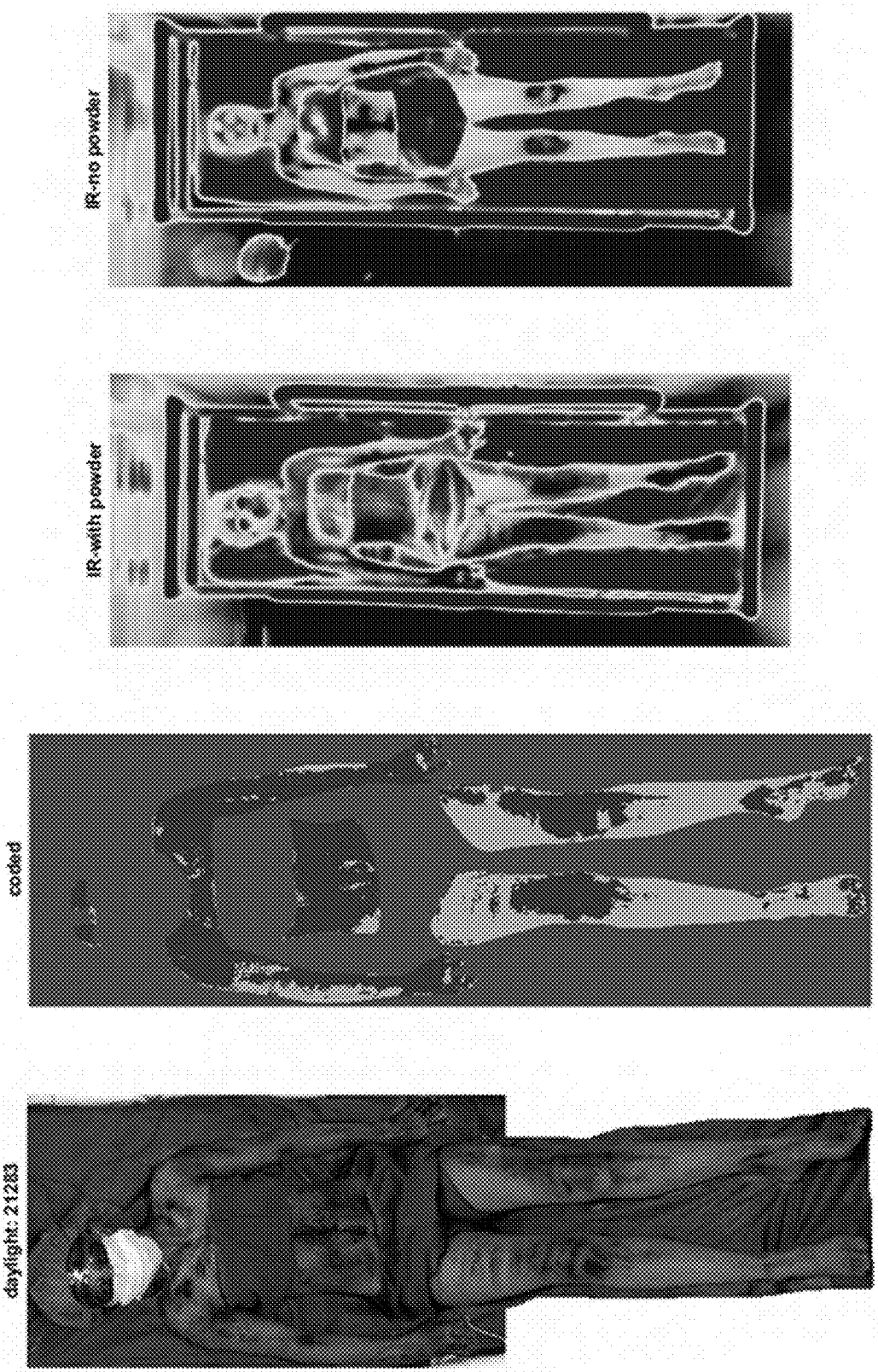

SYSTEMS AND METHODS FOR THERMOREGULATORY SWEAT TESTING

CROSS-REFERENCE TO RELATED PATENT APPLICATION

This application claims priority to and the benefit of U.S. provisional patent application Ser. No. 62/680,099, filed Jun. 4, 2018, which is incorporated herein in its entirety by reference.

Some references, which may include patents, patent applications and various publications, are cited and discussed in the description of this invention. The citation and/or discussion of such references is provided merely to clarify the description of the present invention and is not an admission that any such reference is "prior art" to the invention described herein. All references cited and discussed in this specification are incorporated herein by reference in their entireties and to the same extent as if each reference was individually incorporated by reference. In terms of notation, hereinafter, "[n]" represents the nth reference cited in the reference list. For example, [2] represents the 2nd reference cited in the reference list, namely, Birklein F, Riedl B, Claus D, and Neundorfer B. Pattern of autonomic dysfunction in time course of complex regional pain syndrome. *Clin Auton Res* 8: 79-85, 1998.

FIELD OF THE INVENTION

The present invention relates generally to diagnoses, and more particularly, to systems and methods for the thermoregulatory sweat testing of a living subject.

BACKGROUND OF THE INVENTION

The background description provided herein is for the purpose of generally presenting the context of the invention. The subject matter discussed in the background of the invention section should not be assumed to be prior art merely as a result of its mention in the background of the invention section. Similarly, a problem mentioned in the background of the invention section or associated with the subject matter of the background of the invention section should not be assumed to have been previously recognized in the prior art. The subject matter in the background of the invention section merely represents different approaches, which in and of themselves may also be inventions. Work of the presently named inventors, to the extent it is described in the background of the invention section, as well as aspects of the description that may not otherwise qualify as prior art at the time of filing, are neither expressly nor impliedly admitted as prior art against the invention.

Sweating dysfunction impairs thermoregulatory control in humans. This may be secondary to primary dysfunction of peripheral sweat glands but can also be an indicator of a small fiber neuropathy. Two standard methods are used to assess sudomotor function. One is Q-SWEAT, a quantitative measure of post-ganglionic sudomotor output dependent on local axon reflex stimulation of sweat glands. This method is relatively fast and well-tolerated, but it only tests individual small anatomic regions and is not well suited to evaluating the most distal sites on the body [13]. The second method is the thermoregulatory sweat test (TST), which assesses global distribution of sweating over the body surface with an indicator powder that changes from golden to purple in areas of sweating when subjects reach targetwarming temperature in a humid chamber [13, 15, 22]. TST reveals abnormalities of small sensory and autonomic nerve fiber function which cannot be assessed through standard sensory nerve conduction studies as performed in clinical neurophysiology laboratories. Further, patterns of altered sweating can help identify distal neuropathies and localize pathology to affected spinal nerve roots or peripheral nerves, as shown in FIG. 1.

TST can be central to the identification and management of disorders affecting sudomotor function and small sensory and autonomic nerve fibers, but the cumbersome nature of the standard testing protocol has prevented its widespread adoption. A high resolution, quantitative, clean and simple assay of sweating could significantly improve identification and management of these disorders.

Therefore, a heretofore unaddressed need exists in the art to address the aforementioned deficiencies and inadequacies.

SUMMARY OF THE INVENTION

One of the objectives of this invention is to provide systems and methods for thermoregulatory sweat testing that improve the standard TST methodology.

In one aspect of the invention, the system for thermoregulatory sweat testing of a living subject having a core body temperature includes a chamber for accommodating the living subject, wherein the chamber comprises a heating device for operably elevating the core body temperature of the living subject to a target temperature so as to induce sweating over a skin surface of the living subject; a cooling device for operably creating forced evaporative cooling of the skin surface of the living subject after the core body temperature of the living subject is elevated to the target temperature; an imaging device for acquiring images of the living subject at different times, each image having imaged pixels, the imaging device including one or more infrared cameras, one or more infrared sensors, or a combination of them; and a controller coupled with the chamber and the imaging device for controlling operations of the chamber and the imaging device and processing the acquired images to determine skin surface sweat distributions of the living subject.

In one embodiment, the system further includes at least one probe coupled with the chamber and the controller for operably monitoring a rate of temperature increase and/or ambient heat in the chamber and oral core temperature and/or skin temperature of the living subject, such that when a failsafe mechanism in the chamber, or the oral core temperature or the skin temperature raised beyond a safety threshold values occur, the heating device is turned off. In one embodiment, the at least one probe is configured to further monitor humidity in the chamber.

In one embodiment, the system may also include a display for displaying the surface sweat distributions of the living subject.

In one embodiment, the heating device comprises infrared heat lamps and/or an air convection system.

In one embodiment, the acquired images include one or more images that are acquired after the evaporative cooling is applied to the skin surface of the living subject.

In one embodiment, the skin surface sweat distributions of the living subject is determined by identifying areas of cooling directly from the one or more images, wherein the cooling areas in the one or more images are corresponding to sweating areas of the living subject.

In one embodiment, the acquired images further include a base image that is acquired when the core body temperature of the living subject is elevated to the target temperature and no forced evaporative cooling of the skin surface of the living subject is created. In one embodiment, the skin surface sweat distributions of the living subject is determined by subtracting pixel color values of the one or more images from that of the base image during fan cooling.

In another aspect of the invention, the method for thermoregulatory sweat testing of a living subject having a core body temperature uses a statistical classification method to partially automate the localization of sweating over the body surface when using the standard indicator powder.

In one embodiment, the method includes applying a color-change dye to the living subject; acquiring a first image of the living subject having imaged pixels; elevating the core body temperature of the living subject to a target temperature; acquiring a second image of the living subject having imaged pixels; specifying a linear discriminant classifier based on pixel color values from the first and second images; classifying the imaged pixels as either sweating or non-sweating; counting the number of sweating and non-sweating imaged pixels; and determining a percentage of non-sweating pixels.

In one embodiment, said specifying the linear discriminant classifier comprises defining regions of interest within the first and second images, wherein the regions of interest comprises a body region outlining a body of the living subject in the first and second images; covered regions outlining unobserved areas of the body of the living subject in the first and second images; exemplary dry regions outlining non-sweating areas in the first and second images; and exemplary wet areas outlining color-shifts of the color-change dye in the second image.

In one embodiment, said classifying the imaged pixels comprises using the exemplary dry regions and the exemplary wet areas to train a linear classifier to encode wet and dry regions on a pixel-by-pixel basis within the body region and excluding the covered regions, so as to obtain an encoded image.

In one embodiment, said counting the number of sweating and non-sweating imaged pixels comprises counting the number of wet pixels of the wet regions and the number of dry pixels of the dry regions, respectively, in the encoded image.

In one embodiment, the percentage of non-sweating pixels is calculated by dividing the number of dry pixels by the combined total number of wet and dry pixels in the encoded image.

In yet another aspect of the invention, the method for thermoregulatory sweat testing of a living subject having a core body temperature includes using changes in skin temperature caused by forced evaporative cooling to detect body regions which sweat, which eliminates the use of the indicator powder. Skin areas which produce sweat show a rapid drop in temperature with evaporative cooling induced by fanning compared to those areas without sweat. The thermographic measurements reproduce the spatial resolution of powder-based visible light imaging with less mess and discomfort for the patient.

In one embodiment, the method includes elevating the core body temperature of the living subject to a target temperature; creating forced evaporative cooling of a skin surface of the living subject; and acquiring one or more infrared images of the living subject at different times, each image having imaged pixels; and determining skin surface sweat distributions of the living subject based on the one or more infrared images, wherein cooling areas in the one or more infrared images are corresponding to sweating areas of the living subject.

In one embodiment, said determining the skin surface sweat distributions comprises identifying the cooling areas from the one or more infrared images.

In one embodiment, the method further includes, prior to said creating the forced evaporative cooling of the skin surface of the living subject, acquiring a base infrared image of the living subject having imaged pixels. In one embodiment, said determining the skin surface sweat distributions comprises subtracting pixel color values of the one or more infrared images from that of the base infrared image.

In one embodiment, the skin surface sweat distributions are dynamic spatial temporal characterization of sweat patterns of the living subject.

In a further aspect, the invention relates to a non-transitory tangible computer-readable medium storing instructions which, when executed by one or more processors, cause a system to perform a method for thermoregulatory sweat testing of a living subject having a core body temperature, wherein a skin surface of the living subject is applied with a color-change dye.

In one embodiment, the method comprises acquiring a first image of the living subject having imaged pixels; elevating the core body temperature of the living subject to a target temperature; acquiring a second image of the living subject having imaged pixels; specifying a linear discriminant classifier based on pixel color values from the first and second images; classifying the imaged pixels as either sweating or non-sweating; counting the number of sweating and non-sweating imaged pixels; and determining a percentage of non-sweating pixels.

In one embodiment, said specifying the linear discriminant classifier comprises defining regions of interest within the first and second images, wherein the regions of interest comprises a body region outlining a body of the living subject in the first and second images; covered regions outlining unobserved areas of the body of the living subject in the first and second images; exemplary dry regions outlining non-sweating areas in the first and second images; and exemplary wet areas outlining color-shifts of the color-change dye in the second image.

In one embodiment, said classifying the imaged pixels comprises using the exemplary dry regions and the exemplary wet areas to train a linear classifier to encode wet and dry regions on a pixel-by-pixel basis within the body region and excluding the covered regions, so as to obtain an encoded image.

In one embodiment, said counting the number of sweating and non-sweating imaged pixels comprises counting the number of wet pixels of the wet regions and the number of dry pixels of the dry regions, respectively, in the encoded image.

In one embodiment, the percentage of non-sweating pixels is calculated by dividing the number of dry pixels by the combined total number of wet and dry pixels in the encoded image.

In yet a further aspect, the invention also relates to a non-transitory tangible computer-readable medium storing instructions which, when executed by one or more processors, cause a system to perform a method for thermoregulatory sweat testing of a living subject having a core body temperature. In one embodiment, the method comprises elevating the core body temperature of the living subject to a target temperature; creating forced evaporative cooling of a skin surface of the living subject; and acquiring one or more infrared images of the living subject at different times, each image having imaged pixels; and determining skin surface sweat distributions of the living subject based on the one or more infrared images, wherein cooling areas in the one or more infrared images are corresponding to sweating areas of the living subject.

In one embodiment, said determining the skin surface sweat distributions comprises identifying the cooling areas from the one or more infrared images.

In one embodiment, the method further comprises, prior to said creating the forced evaporative cooling of the skin surface of the living subject, acquiring a base infrared image of the living subject having imaged pixels.

In one embodiment, said determining the skin surface sweat distributions comprises subtracting pixel color values of the one or more infrared images from that of the base infrared image.

These and other aspects of the present invention will become apparent from the following description of the preferred embodiment taken in conjunction with the following drawings, although variations and modifications therein may be affected without departing from the spirit and scope of the novel concepts of the disclosure.

BRIEF DESCRIPTION OF THE DRAWINGS

The patent or application filed contains at least one drawing executed in color. Copies of this patent or patent application publication with color drawing(s) will be provided by the office upon request and payment of the necessary fee.

The accompanying drawings illustrate one or more embodiments of the invention and together with the written description, serve to explain the principles of the invention. Wherever possible, the same reference numbers are used throughout the drawings to refer to the same or like elements of an embodiment.

FIGS. 5A-5E show accuracy and consistency of correlations between indicator powder and thermography derived results across all patients according to embodiments of the invention. Receiver operating characteristic (ROC) area under the curve (AUC, FIG. 5A) as a function of age (females, orange; males, cyan). Threshold temperatures (FIG. 5B) producing the best classification accuracy. Sweat distribution likelihood normalized to a schematic body figure (FIG. 5C; scale: probability), mean spatial distribution of skin temperature (FIG. 5D; scale: ° C.), and spatial correlation between sweating and cooling (FIG. 5E; scale: as positive correlation coefficient).

FIG. 7A shows a daylight image using color change dye after heating, where purple areas indicate sweating. FIG. 7B shows sweating areas encoded using linear discriminant analysis from exemplar regions, processed from the image of FIG. 7A. FIG. 7C shows an infrared imaging after heating and then fan cooling during the same test as shown in FIGS. 7A-7B, with color change powder, where cool colors (blue tones) indicate cooler regions (presumed areas of sweating). FIG. 7D shows repeat testing with infrared imaging and no color change powder used.

FIGS. 8A-8D show performance and reproducibility of infrared imaging of evaporative cooling as a substitute for color change powder according to embodiments of the invention. FIG. 8A shows a daylight image using color change dye after heating, where purple areas indicate sweating. FIG. 8B shows sweating areas encoded using linear discriminant analysis from exemplar regions, processed from the image of FIG. 8A. FIG. 8C shows an infrared imaging after heating and then fan cooling during the same test as shown in FIGS. 8A-8B, with color change powder, where cool colors (blue tones) indicate cooler regions (presumed areas of sweating). FIG. 8D shows repeat testing with infrared imaging and no color change powder used.

FIG. 9A shows a daylight image using color change dye after heating, where purple areas indicate sweating. FIG. 9B shows sweating areas encoded using linear discriminant analysis from exemplar regions, processed from the image of FIG. 9A. FIG. 9C shows an infrared imaging after heating and then fan cooling during the same test as shown in FIGS. 9A-9B, with color change powder, where cool colors (blue tones) indicate cooler regions (presumed areas of sweating). FIG. 9D shows repeat testing with infrared imaging and no color change powder used.

FIG. 10A shows a daylight image using color change dye after heating, where purple areas indicate sweating. FIG. 10B shows sweating areas encoded using linear discriminant analysis from exemplar regions, processed from the image of FIG. 10A. FIG. 10C shows an infrared imaging after heating and then fan cooling during the same test as shown in FIGS. 10A-10B, with color change powder, where cool colors (blue tones) indicate cooler regions (presumed areas of sweating). FIG. 10D shows repeat testing with infrared imaging and no color change powder used.

FIG. 11A shows a daylight image using color change dye after heating, where purple areas indicate sweating. FIG. 11B shows sweating areas encoded using linear discriminant analysis from exemplar regions, processed from the image of FIG. 11A. FIG. 11C shows an infrared imaging after heating and then fan cooling during the same test as shown in FIGS. 11A-11B, with color change powder, where cool colors (blue tones) indicate cooler regions (presumed areas of sweating). FIG. 11D shows repeat testing with infrared imaging and no color change powder used.

FIG. 12A shows a daylight image using color change dye after heating, where purple areas indicate sweating. FIG. 12B shows sweating areas encoded using linear discriminant analysis from exemplar regions, processed from the image of FIG. 12A. FIG. 12C shows an infrared imaging after heating and then fan cooling during the same test as shown in FIGS. 12A-12B, with color change powder, where cool colors (blue tones) indicate cooler regions (presumed areas of sweating). FIG. 12D shows repeat testing with infrared imaging and no color change powder used.

DETAILED DESCRIPTION OF THE INVENTION

Figure 1:
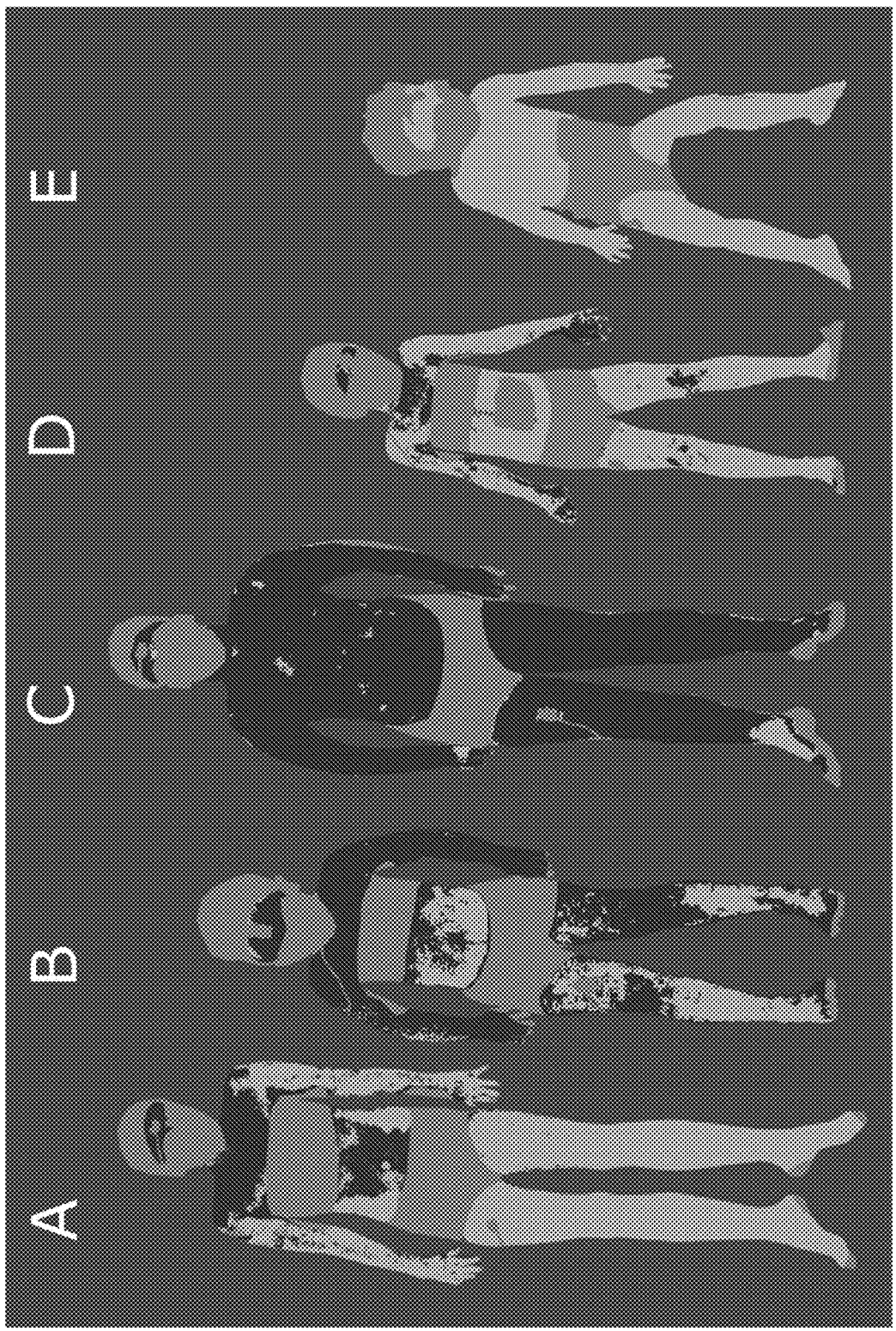
FIG. 1 shows representative clinical findings in thermoregulatory sweat testing for a 13 yo (years old) girl (A) with normal strength, muscle stretch reflexes, motor and sensory nerve conduction studies, who presented with neuropathic pain from a length-dependent small fiber peripheral neuropathy, a 9 yo boy (B) with orthostatic dizziness, gastrointestinal (GI) dysmotility and assymetric neuropathic pain (greater on the right lower extremity), who was diagnosed with seronegative autoimmune ganglionopathy, a 14 yo boy (C) with abdominal pain, GI dysmotility, which TST results are normal except for focal anhidrosis around the medial right ankle at the site previous injury, a 9 yo girl (D) with GI dysmotility, abdominal pain and 83% anhidrosis on TST, which peripheral nerve pathology was confirmed with results of Q-SWEAT volume on right extremities, and a 3 yo girl (E) with global developmental delay, poor sleep and unexplained fevers, where a chromosomal microarray demonstrated a rare microdeletion associated with neurodevelopmental disorders.

The present invention will now be described more fully hereinafter with reference to the accompanying drawings, in which exemplary embodiments of the present invention are shown. The present invention may, however, be embodied in many different forms and should not be construed as limited to the embodiments set forth herein. Rather, these embodiments are provided so that this disclosure will be thorough and complete, and will fully convey the scope of the invention to those skilled in the art. Like reference numerals refer to like elements throughout.

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. For convenience, certain terms may be highlighted, for example using italics and/or quotation marks. The use of highlighting and/or capital letters has no influence on the scope and meaning of a term; the scope and meaning of a term are the same, in the same context, whether or not it is highlighted and/or in capital letters. It will be appreciated that the same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification, including examples of any terms discussed herein, is illustrative only and in no way limits the scope and meaning of the invention or of any exemplified term. Likewise, the invention is not limited to various embodiments given in this specification.

It will be understood that, although the terms first, second, third, etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below can be termed a second element, component, region, layer or section without departing from the teachings of the present invention.

It will be understood that, as used in the description herein and throughout the claims that follow, the meaning of "a", "an", and "the" includes plural reference unless the context clearly dictates otherwise. Also, it will be understood that when an element is referred to as being "on," "attached" to, "connected" to, "coupled" with, "contacting," etc., another element, it can be directly on, attached to, connected to, coupled with or contacting the other element or intervening elements may also be present. In contrast, when an element is referred to as being, for example, "directly on," "directly attached" to, "directly connected" to, "directly coupled" with or "directly contacting" another element, there are no intervening elements present. It will also be appreciated by those of skill in the art that references to a structure or feature that is disposed "adjacent" to another feature may have portions that overlap or underlie the adjacent feature.

It will be further understood that the terms "comprises" and/or "comprising," or "includes" and/or "including" or "has" and/or "having" when used in this specification specify the presence of stated features, regions, integers, steps, operations, elements, and/or components, but do not preclude the presence or addition of one or more other features, regions, integers, steps, operations, elements, components, and/or groups thereof.

Furthermore, relative terms, such as "lower" or "bottom" and "upper" or "top," may be used herein to describe one element's relationship to another element as illustrated in the figures. It will be understood that relative terms are intended to encompass different orientations of the device in addition to the orientation shown in the figures. For example, if the device in one of the figures is turned over, elements described as being on the "lower" side of other elements would then be oriented on the "upper" sides of the other elements. The exemplary term "lower" can, therefore, encompass both an orientation of lower and upper, depending on the particular orientation of the figure. Similarly, if the device in one of the figures is turned over, elements described as "below" or "beneath" other elements would then be oriented "above" the other elements. The exemplary terms "below" or "beneath" can, therefore, encompass both an orientation of above and below.

Unless otherwise defined, all terms (including technical and scientific terms) used herein have the same meaning as commonly understood by one of ordinary skill in the art to which the present invention belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

As used in this disclosure, "around", "about", "approximately" or "substantially" shall generally mean within 20 percent, preferably within 10 percent, and more preferably within 5 percent of a given value or range. Numerical quantities given herein are approximate, meaning that the term "around", "about", "approximately" or "substantially" can be inferred if not expressly stated.

As used in this disclosure, the phrase "at least one of A, B, and C" should be construed to mean a logical (A or B or C), using a non-exclusive logical OR. As used herein, the term "and/or" includes any and all combinations of one or more of the associated listed items.

The description below is merely illustrative in nature and is in no way intended to limit the invention, its application, or uses. The broad teachings of the invention can be implemented in a variety of forms. Therefore, while this invention includes particular examples, the true scope of the invention should not be so limited since other modifications will become apparent upon a study of the drawings, the specification, and the following claims. For purposes of clarity, the same reference numbers will be used in the drawings to identify similar elements. It should be understood that one or more steps within a method may be executed in different order (or concurrently) without altering the principles of the invention.

One of the objectives of this invention is to provide systems and methods for thermoregulatory sweat testing of a living subject, which improve the standard TST methodology.

Figure 13:
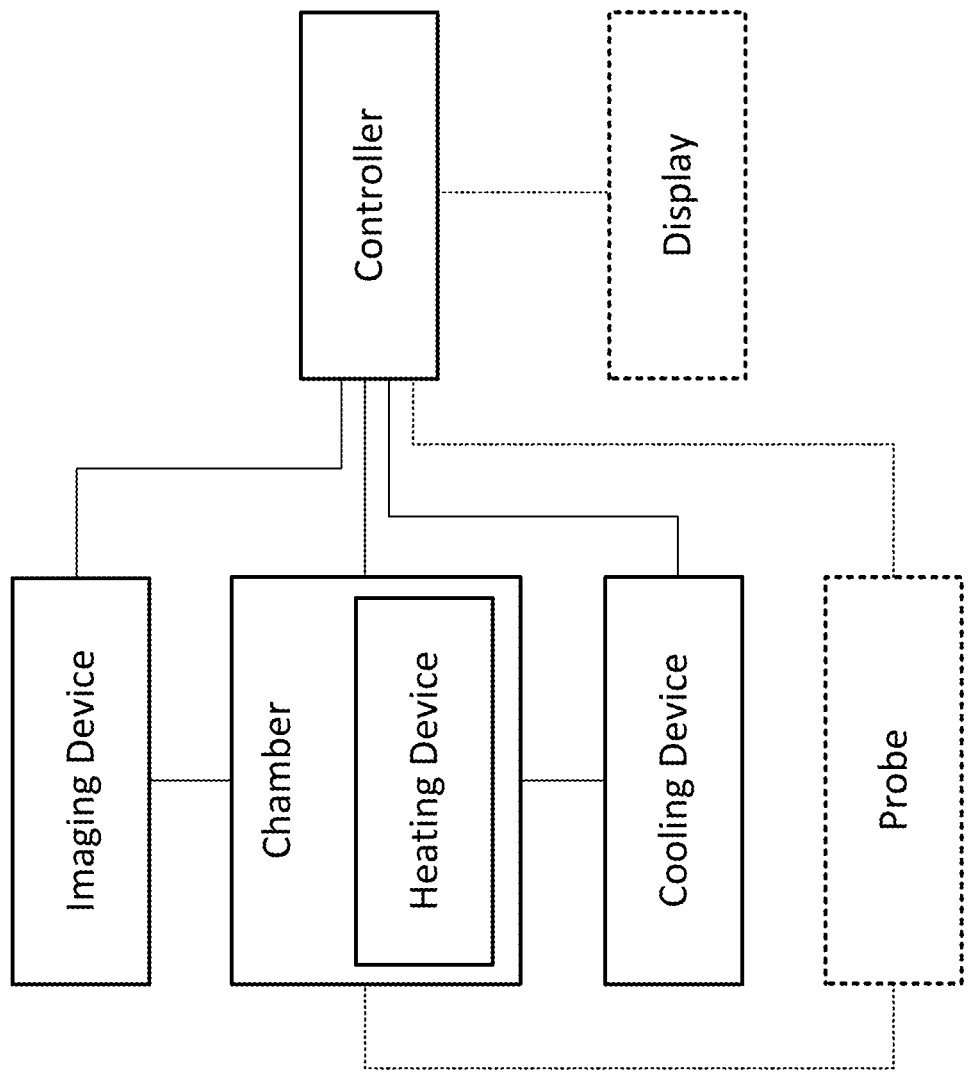
FIG. 13 shows schematically a system for thermoregulatory sweat testing of a living subject according to embodiments of the invention.

Referring to FIG. 13, the system for thermoregulatory sweat testing of a living subject is shown according to embodiments of the invention.

The system includes a chamber for accommodating the living subject. The chamber comprises a heating device for operably elevating the core body temperature of the living subject to a target temperature so as to induce sweating over a skin surface of the living subject. The target temperature is a temperature at which or above of which the living subject starts sweating and/or sweats. The target temperature may be different for different living subjects.

The system further includes an imaging device for acquiring images of the living subject at different times, each image having imaged pixels.

In addition, the system also includes a controller coupled with the chamber and the imaging device for controlling operations of the chamber and the imaging device and processing the acquired images to determine skin surface sweat distributions of the living subject.

In one embodiment, the system may further include a probe coupled with the chamber and the controller for operably monitoring a rate of temperature increase and/or ambient heat in the chamber and oral core temperature and/or skin temperature of the living subject, such that when a failsafe mechanism in the chamber, or the oral core temperature or the skin temperature raised beyond a safety threshold values occur, the heating device is turned off. In one embodiment, the probe is configured to further monitor humidity in the chamber.

In one embodiment, the system may also include a display for displaying the surface sweat distributions of the living subject.

In one embodiment, the heating device comprises infrared heat lamps. Potentially an air convection system could be used but probably wouldn't raise the skin temperature as quickly. The room is preheated using conventional HVAC to raise the ambient temperature somewhat in preparation for the test.

In one embodiment, the skin surface of the living subject is applied with a color-change dye.

In one embodiment, the imaging device comprises one or more visible light cameras, one or more visible light sensors, or a combination of them.

In one embodiment, the acquired images include a first image that is acquired before the heating device is turned on; and a second image that is acquired after the heating device is turned on and when the core body temperature of the living subject is elevated to the target temperature.

In one embodiment, the acquired images are processed by specifying a linear discriminant classifier based on pixel color values from the first and second images; classifying the imaged pixels as either sweating or non-sweating; counting the number of sweating and non-sweating imaged pixels; and determining a percentage of non-sweating pixels.

In one embodiment, said specifying the linear discriminant classifier using regions of interest defined within the first and second images. The regions of interest comprises a body region outlining a body of the living subject in the first and second images; covered regions outlining unobserved areas of the body of the living subject in the first and second images; and exemplary dry regions outlining non-sweating areas in the first and second images; and exemplary wet areas outlining color-shifts of the color-change dye in the second image. In certain embodiment, the regions of interest can be defined by a human technician, or a computer program.

In one embodiment, said classifying the imaged pixels comprises using the exemplary dry regions and the exemplary wet areas to train a linear classifier to encode wet and dry regions on a pixel-by-pixel basis within the body region and excluding the covered regions, so as to obtain an encoded image.

In one embodiment, said counting the number of sweating and non-sweating imaged pixels comprises counting the number of wet pixels of the wet regions and the number of dry pixels of the dry regions, respectively, in the encoded image.

In one embodiment, the percentage of non-sweating pixels is calculated by dividing the number of dry pixels by the combined total number of wet and dry pixels in the encoded image.

In one embodiment, the system further has a cooling device for operably creating forced evaporative cooling of the skin surface of the living subject after the core body temperature of the living subject is elevated to the target temperature. In one embodiment, the cooling device comprises one or more fans.

In one embodiment, the imaging device comprises one or more infrared cameras, one or more infrared sensors, or a combination of them.

In one embodiment, the acquired images include one or more images that are acquired after the evaporative cooling is applied to the skin surface of the living subject.

In one embodiment, the skin surface sweat distributions of the living subject is determined by identifying areas of cooling directly from the one or more images, wherein the cooling areas in the one or more images are corresponding to sweating areas of the living subject.

In one embodiment, the acquired images further include a base image that is acquired when the core body temperature of the living subject is elevated to the target temperature and no forced evaporative cooling of the skin surface of the living subject is created. In one embodiment, the skin surface sweat distributions of the living subject is determined by subtracting pixel color values of the one or more images from that of the base image.

In one aspect of the invention, the method for thermoregulatory sweat testing of a living subject having a core body temperature uses a statistical classification method to partially automate the localization of sweating over the body surface when using the standard indicator powder.

In one embodiment, the method includes applying a color-change dye to the living subject; acquiring a first image of the living subject having imaged pixels; elevating the core body temperature of the living subject to a target temperature; acquiring a second image of the living subject having imaged pixels; specifying a linear discriminant classifier based on pixel color values from the first and second images; classifying the imaged pixels as either sweating or non-sweating; counting the number of sweating and non-sweating imaged pixels; and determining a percentage of non-sweating pixels.

In one embodiment, said specifying the linear discriminant classifier is performed using regions of interest defined within the first and second images. The regions of interest comprises a body region outlining a body of the living subject in the first and second images; covered regions outlining unobserved areas of the body of the living subject in the first and second images; exemplary dry regions outlining non-sweating areas in the first and second images; and exemplary wet areas outlining color-shifts of the color-change dye in the second image. In certain embodiment, the regions of interest can be defined by a human technician, or a computer program.

In one embodiment, said classifying the imaged pixels comprises using the exemplary dry regions and the exemplary wet areas to train a linear classifier to encode wet and dry regions on a pixel-by-pixel basis within the body region and excluding the covered regions, so as to obtain an encoded image.

In one embodiment, said counting the number of sweating and non-sweating imaged pixels comprises counting the number of wet pixels of the wet regions and the number of dry pixels of the dry regions, respectively, in the encoded image.

In one embodiment, the percentage of non-sweating pixels is calculated by dividing the number of dry pixels by the combined total number of wet and dry pixels in the encoded image.

In another aspect of the invention, the method for thermoregulatory sweat testing of a living subject having a core body temperature includes using changes in skin temperature caused by forced evaporative cooling to detect body regions which sweat, which eliminates the use of the indicator powder. Skin areas which produce sweat show a rapid drop in temperature with evaporative cooling induced by fanning compared to those areas without sweat. The thermographic measurements reproduce the spatial resolution of powder-based visible light imaging with less mess and discomfort for the patient.

In one embodiment, the method includes elevating the core body temperature of the living subject to a target temperature; creating forced evaporative cooling of a skin surface of the living subject; and acquiring one or more infrared images of the living subject at different times, each image having imaged pixels; and determining skin surface sweat distributions of the living subject based on the one or more infrared images, wherein cooling areas in the one or more infrared images are corresponding to sweating areas of the living subject.

In one embodiment, said determining the skin surface sweat distributions comprises identifying the cooling areas from the one or more infrared images.

In one embodiment, the method further includes, prior to said creating the forced evaporative cooling of the skin surface of the living subject, acquiring a base infrared image of the living subject having imaged pixels. In one embodiment, said determining the skin surface sweat distributions comprises subtracting pixel color values of the one or more infrared images from that of the base infrared image.

In one embodiment, the skin surface sweat distributions are dynamic spatial temporal characterization of sweat patterns of the living subject.

Briefly, the first innovation is a method for using a semi-automated algorithm to characterize sweat distributions using the current indicator dye powder. In this method, a user identifies exemplar regions of sweating and non-sweating in a set of two daylight images taken of a patient before and after an evoked increase in core body temperature. Pixel color values from the exemplar regions are used to specify a linear discriminant classifier, which is then used to classify all the imaged pixels as either sweating or non-sweating. Counts of wet and dry pixels are then used to calculate the clinically relevant percent anhidrosis (percent of non-sweating).

The second innovation involves using an infrared imaging camera without indicator dye powder. After the patient's core temperature is raised to threshold, fans are used to create forced evaporative cooling of the patient's skin, with sweating areas cooling more than dry areas. Areas of cooling can be identified directly in the images taken after cooling or (with patient cooperation) from image subtraction methods. Using a temperature change threshold, these analyses can be used to generate a proxy for percent anhidrosis.

In certain exemplary embodiments, images from 89 clinical TSTs were analyzed retrospectively using the above-disclosed methods. Correlation and receiver operating characteristic analyses were used to determine the degree of match between these methods, and the potential limits of thermal imaging were examined through cumulative analysis of all studied patients. Algorithmic encoding of sweating and non-sweating regions produces a more objective analysis for clinical decision making. Additionally, results from the forced cooling method correspond well with those from indicator powder imaging, with a correlation across spatial regions of −0.78 (CI: −0.84 to −0.71). The method works similarly across body regions, and frame-by-frame analysis suggests the ability to identify sweating regions within about 1 second of imaging. While algorithmic encoding can enhance the standard sweat testing protocol, thermal imaging with forced evaporative cooling can dramatically improve the TST by making it less time-consuming and more patient-friendly than the current approach.

In one aspect, the method provides a more objective, semi-automated method of identifying sweat patterns during testing with an indicator dye powder (exemplar-based objective sweat localization: EOSL). In another aspect, the new imaging modality (infrared imaging of forced evaporative cooling) allows sweat assessment without using the indicator dye powder at all (stainless thermoregulatory testing: STT). Furthermore, the method may allow faster, more accurate imaging of sweating patterns.

According to the invention, the novel methods can be employed for, among other things, early identification, diagnosis and management of primary neurological disorders as well as those secondary to other illnesses; identification of areas of sweating as an indicator of autonomic activation, possibly as an indicator of autonomic dysfunction or illness; and/or identification of areas of sweating as an indicator of autonomic activation, possibly as an indicator of emotional arousal due to psychological stress.

The invented methods also improve the test, allowing more broad adoption in detection, diagnosis and management of these disorders. Such a system could allow testing of much larger populations of patients in more locations (rather than the handful of adult specialty hospitals that handle the testing now).

It should be noted that all or a part of the steps according to the embodiments of the present invention is implemented by hardware or a program instructing relevant hardware, or any combination thereof. Yet another aspect of the invention provides a non-transitory tangible computer-readable medium storing instructions which, when executed by one or more processors, cause a system to perform the above disclosed methods for thermoregulatory sweat testing of a living subject having a core body temperature. The computer executable instructions or program codes enable a computer or a similar computing system to complete various operations in the above disclosed method for thermoregulatory sweat testing of a living subject. Storage media may be any available media that can be accessed by a computer. By way of example, and not limitation, such computer-readable media can comprise a random-access memory (RAM), a read-only memory (ROM), an electrically erasable programmable ROM (EEPROM), optical disk storage, magnetic disk storage, other magnetic storage devices, combinations of the aforementioned types of computer-readable media, or any other medium that can be used to store computer executable code in the form of instructions or data structures that can be accessed by a computer.

These and other aspects of the present invention are further described below. Without intent to limit the scope of the invention, exemplary instruments, apparatus, methods and their related results according to the embodiments of the present invention are given below. Note that titles or subtitles may be used in the examples for convenience of a reader, which in no way should limit the scope of the invention. Moreover, certain theories are proposed and disclosed herein; however, in no way they, whether they are right or wrong, should limit the scope of the invention so long as the invention is practiced according to the invention without regard for any particular theory or scheme of action.

Example 1

Novel Methods of Imaging and Analysis for Thermoregulatory Sweat Testing

In this exemplary study, we disclose novel methods that improve the standard TST methodology. The first uses a statistical classification method to partially automate the localization of sweating over the body surface when using the standard indicator powder. The second includes using changes in skin temperature caused by forced evaporative cooling to detect body regions which sweat, an approach that could eliminate the use of the indicator powder. Skin areas which produce sweat show a rapid drop in temperature with evaporative cooling induced by fanning compared to those areas without sweat. The thermographic measurements reproduce the spatial resolution of powder-based visible light imaging with less mess and discomfort for the patient.

The techniques described here were developed from the Ann & Robert H. Lurie Children's Hospital of Chicago clinical protocol for TST (which is based on the Mayo Clinic protocol) [13]. Briefly, patients lay supine on a gurney outside of the testing chamber wearing disposable paper swimming trunks (and tube top for females), paper head cover, eye goggles, and a face mask.

Alizarin-based indicator powder is sprinkled on their skin, and skin surface and core temperature probes are placed. The patient and gurney are then rolled into a preheated custom-designed thermoregulatory chamber (built as a partnership between DMC, Inc. and Lurie Children's Hospital Center for Autonomic Medicine in Pediatrics). Sweating is induced with a protocol that raises core body temperature using a humid warming chamber and infrared heat lamps. Both ambient heat and humidity are controlled in the chamber. Additionally, overhead radiant heat lamps are used to provide additional heat, which gradually raises the patient's core body temperature during testing by at least 1° C. or to 38° C., whichever is higher. Upon reaching this target core body temperature, well-hydrated individuals sweat over all exposed body surface regions. Presence of sweat gland abnormalities, autonomic dysfunction in control pathways for sweating (hypothalamus through peripheral autonomic fibers) and/or medications which inhibit sweating will produce TST abnormalities. The heat lamps are controlled by a custom servo-control system taking inputs from the axillary and oral core temperature probes as well as the skin surface temperature probes. The system allows precise control over the rate of temperature increase as well as a failsafe mechanism that shuts down the heat lamps if temperature probes are disconnected or skin temperature rises beyond a safety threshold value. Though the chamber and heating protocol are based on that developed at Mayo Clinic Rochester [13]. Lurie Children's Hospital TST was created with children in mind. There is extra space in the chamber for a caretaker or staff member to accompany the child during testing. The sides of the chamber are windowed to minimize potential for claustrophobia and allow visualization of an entertainment wall monitor. Standard videography and photography are used to record powder color change. At completion of standard testing, a hand-held fan is used to rapidly return the patient to a more comfortable temperature. During cooling, a high-resolution ceiling-mounted infrared imaging camera documents skin surface temperature. After fan cooling, the patient is then allowed to shower in order to remove the indicator powder.

Study Cohort:

This study is a retrospective review of TST data from 89 tests of 87 unique individuals referred for clinical testing. The average age at the time of testing was 14.1 years old (range 4.8 to 43.2 years old; standard deviation: 5.3), with 28 males and 59 females. Referral conditions included: fatigue or autonomic dysfunction (30 patients); orthostatic complaints such as dizziness or syncope (21 patients); neuropathy or paresthesias (12 patients); abdominal pain, nausea or vomiting (11 patients); diffuse pain (10 patients) and other conditions (3 patients).

Figures 2A, 2B, 2C, 2D:
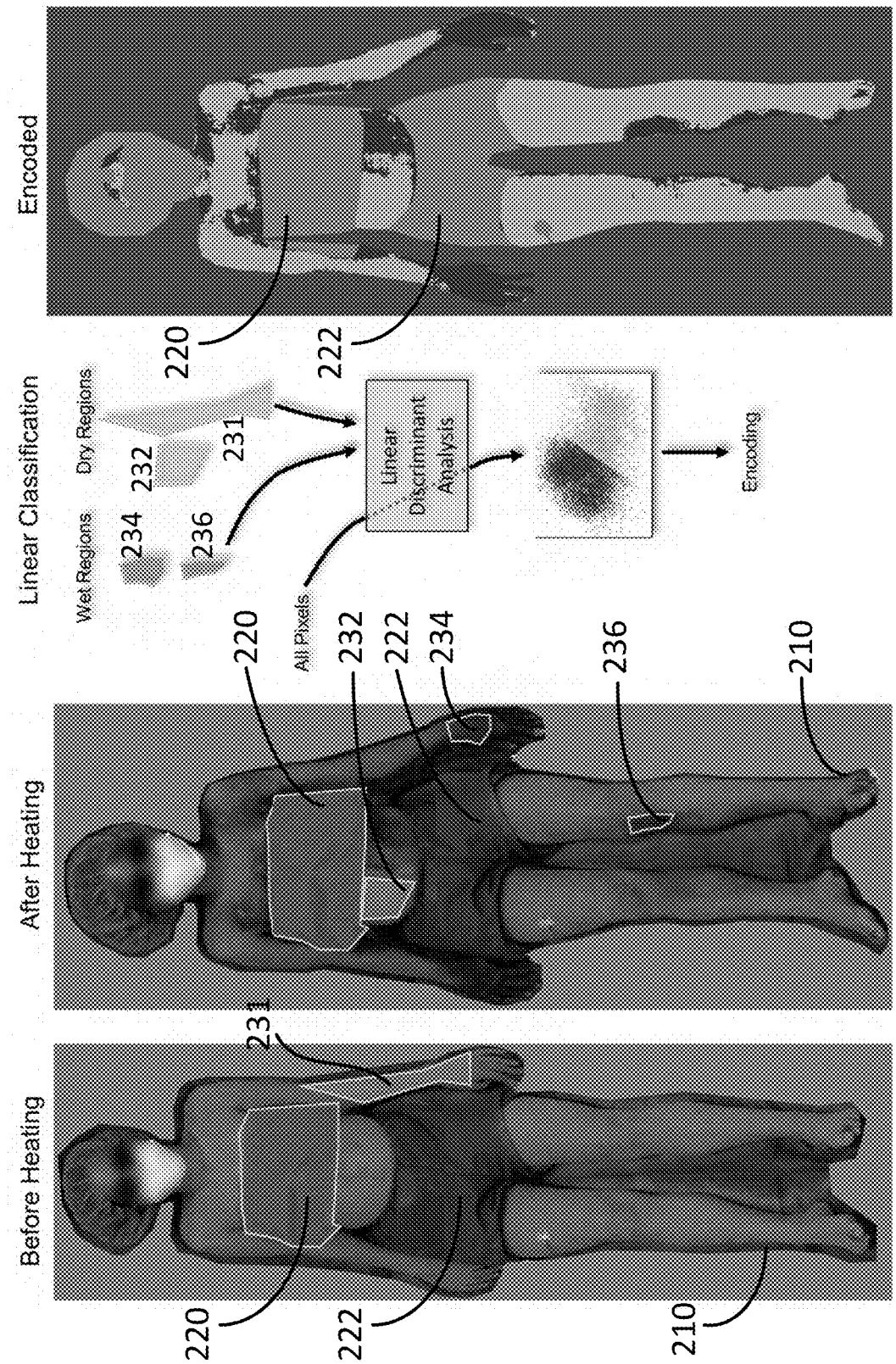
FIGS. 2A-2D show semi-automatic classification of skin surface sweating according to embodiments of the invention. Images before (FIG. 2A) and after (FIG. 2B) heating used to define outline, covered areas (gray) and example areas of sweating (wet, purple) or non-sweating (dry, yellow). Example regions are used to train a linear discriminant classifier (FIG. 2C), from which all pixels in the image are encoded as sweating or non-sweating (FIG. 2D).

Traditional Protocol with Novel Analysis by Color-Change Powder:

In preparing the TST clinical report, the traditional protocol requires a trained technologist to manually record sweating and non-sweating areas on a schematic body outline using a digital paint program to normalize post-heating images from digital cameras mounted on the ceiling of the thermoregulatory chamber. In one aspect of the invention, the novel encoding method allows semi-automated objective classification of wet and dry regions over the skin surface without this manual (and subjective) process. In the Lurie Children's Hospital protocol, regions of interest within the pre- and post-heating images are defined using the ImageJ Java-based image processing application as follows: a single region 210 following the outline of the body; excluded regions 220 and 222 defining unobserved areas; and a small number of example regions 321 and 232 outlining non-sweating areas (both before and after heating) along with wet areas 234 and 236 defined by a purple shift in the indicator dye, as shown in FIGS. 2A-2B. The example regions 231, 232, 234, and 236 are then used to train a linear classifier to encode wet and dry regions on a pixel-by-pixel basis (FIG. 2C) within the body outline 210 and exclude the unobserved (covered) regions 220 and 222 shown in gray in FIG. 2D. The final image shown in FIG. 2D is then used to calculate percent anhidrosis over the observed area as the number of 'dry' pixels divided by the combined total of 'wet' and 'dry' pixels. The percent anhidrosis measure, along with the encoded image, is used for clinical reporting.

Figure 3C:
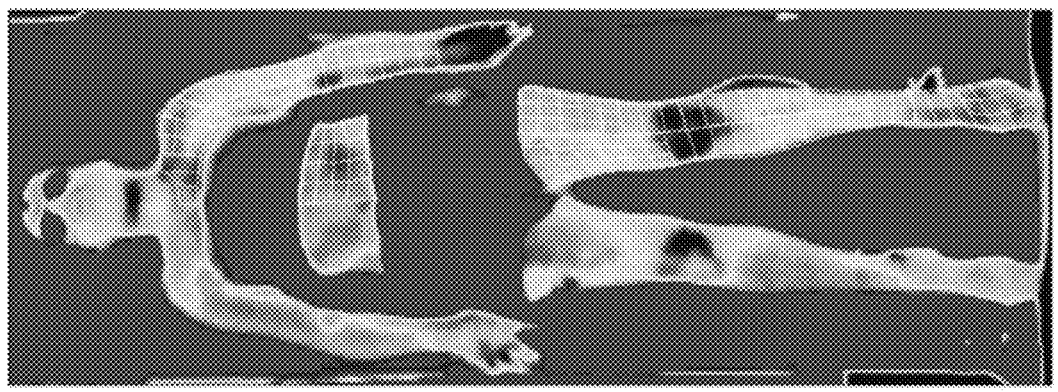
FIGS. 3A-3E show examples of visible light dye encoded diaphoresis with infrared imaging after forced evaporative cooling according to embodiments of the invention. Composite visible light image (FIG. 3A) with areas of purple indicating local sweating, encoding of this sweat distribution with a semiautomatic algorithm (FIG. 3B), and infrared image after fan cooling (FIG. 3C). Sampled regions over the body surface show a negative correlation (FIG. 3D) between fan-cooled skin temperature and encoded pattern of diaphoresis. The accuracy of classifying regions under a given temperature threshold as wet over a range of thresholds is depicted in a receiver operating characteristic (ROC) curve (FIG. 3E).
Figure 3B:
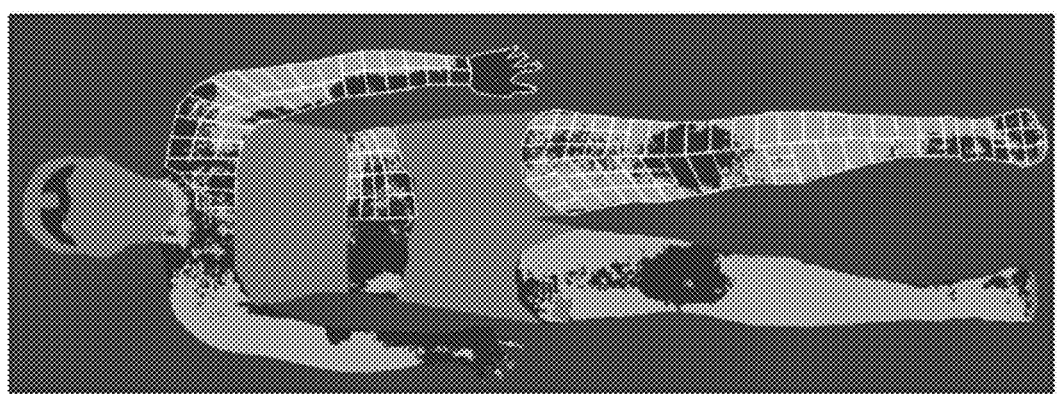
Figure 3A:
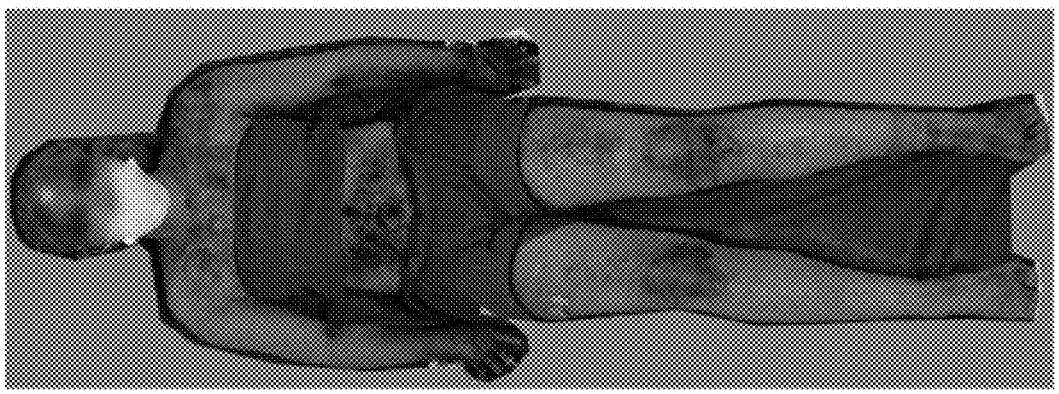

Comparison of Novel Analysis by Color-Change Powder with Infrared Images:

For the purposes of the current study, these wet/dry encoded images were compared with images taken from a ceiling-mounted infrared camera. Because the location and optics of this camera (above umbilicus) differed from the visible light cameras (above head and feet) used for color change classification, a method of approximately reconciling these images was developed. Anatomical landmarks in the visible light and infrared images were used to manually define 29 skin surface regions for visible light and infrared images. For example, arms and legs were divided into proximal and distal segments at the elbows and knees. These were further subdivided into medial and lateral areas. The torso was similarly divided laterally and along the sagittal plane. To supplement this coarse-grained analysis using relatively large skin surface regions, an automated method (custom script in MATLAB) was used to geometrically subdivide these manually-defined regions into corresponding smaller areas, as shown in FIGS. 3B and 3C. Because of geometric complexity, left and right hands, and two regions that included irregular exclusion areas for skin surface temperature probes (forehead and lateral right leg) were not further subdivided.

Using the standard indicator powder method, skin surface sweat distributions were determined algorithmically from a sample of wet and dry regions for each patient. In order to analyze the usefulness of thermal imaging of forced evaporative cooling as an alternative method, spatially localized sweat patterns as determined by the change in color of the indicator was compared with skin surface temperature changes using a method of geometrically subdividing corresponding anatomical regions.

Figure 3D:
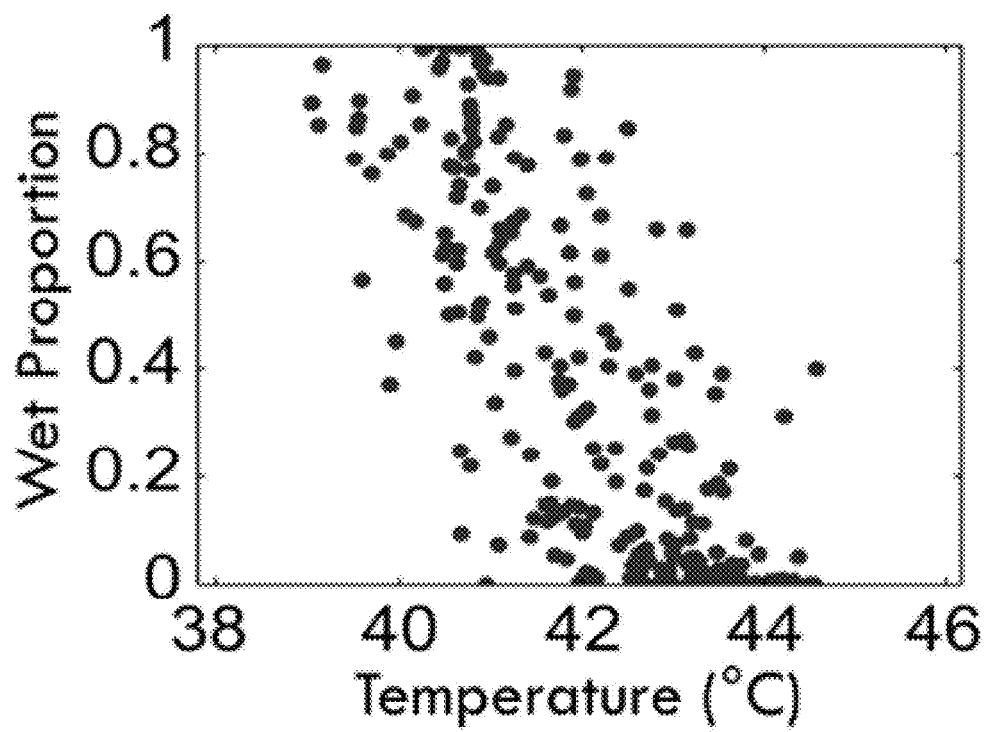
Figure 3E:
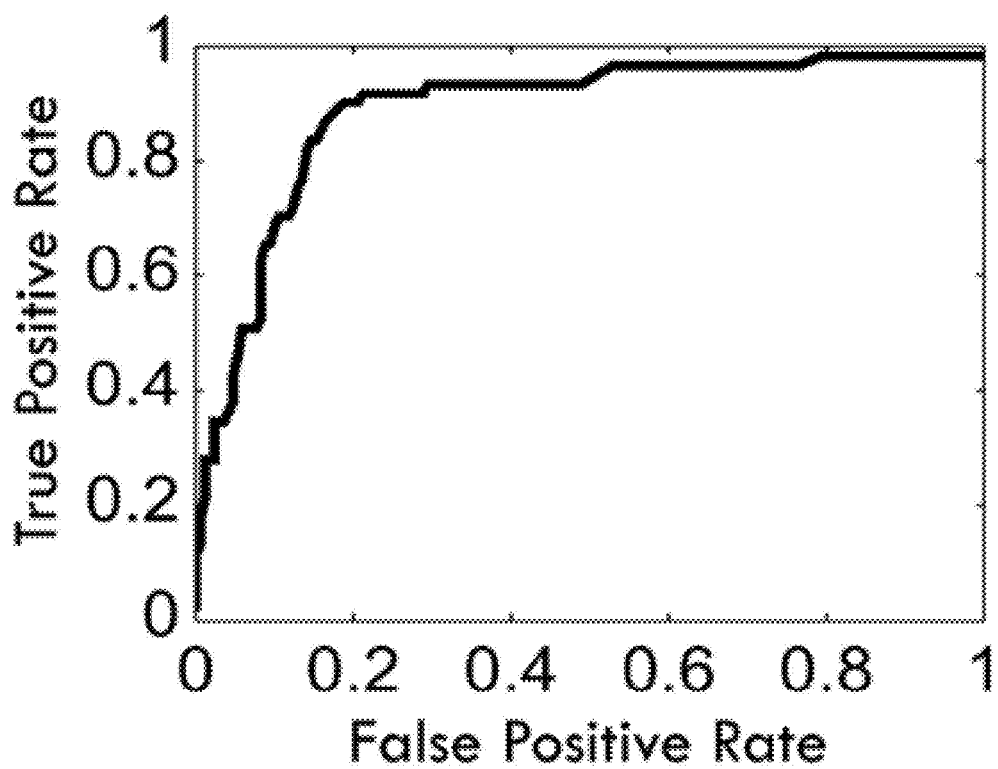

In this way, thermal images and wet/dry coded visible light images taken from different angles could be compared and reconciled to determine the relationship between skin surface evaporative cooling and sweat distribution during the test. The proportion of pixels within each subregion classified as 'wet' was calculated along with the mean temperature within the corresponding region in the thermal images. An example of the relationship between skin temperature and the wet proportion is shown in FIG. 3D, where the correlation coefficient is −0.78 (confidence intervals (CI): −0.84 to −0.71; significance based on 10,000 bootstrap samples, alpha=0.05). To further examine the ability of the temperature profile to act as a proxy for the indicator powder, a receiver operating characteristic curve (ROC) was calculated for each test. The ROC curve characterizes the trade-off between sensitivity and specificity in correctly classifying an observation along the range of possible thresholds. In this case, the range of temperature thresholds used to define wet/dry regions is scanned, and the true positive rate (proportion of regions designated as wet by both the thermal and color analyses) and false positive rate (those incorrectly identified as wet from thermal analysis) are calculated. This analysis (as exemplified in FIG. 3E) produces a line within the [0, 1] domain where good classification accuracy is characterized by a curve arcing up and to the left. Integrating the area under the curve (AUC) provides a single metric of accuracy in binary classification problems. In this figure example, the AUC is 0.922 (CI: 0.888 to 0.956).

The region splitting method described above was necessary to reconcile visible light images taken with one set of cameras with images from the infrared camera with different placement and optics. It was also needed to be able to match and compare infrared images before fan cooling with those after fan cooling even if the patient moved. In the absence of patient movement, a much simpler image subtraction method would show the topography of cooling across the skin surface. In order to estimate the limits of such a method, a series of infrared images were analyzed frame by frame as a subtraction from a baseline image. Each image therefore quantified the temperature change caused by evaporative cooling as the fan airflow passed over the patient's body. Six regions of sweating and non-sweating were identified from the corresponding indicator powder image, and temperature changes over those regions were calculated for 4 infrared video frames (2 seconds).

Figure 4A:
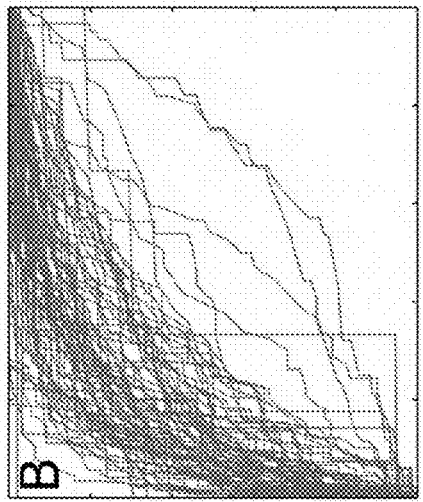
FIGS. 4A-4D show receiver operating characteristic (ROC) classification curves for using thermal imaging to identify sweating in all patients at time of maximal heating (FIG. 4A), after cooling (FIG. 4B) and for the region by region difference in temperature during fan cooling (FIG. 4C) according to embodiments of the invention. Average ROC curves across patients for each method (FIG. 4D) with marker colors matched from FIGS. 4A-4C (Vertical marker length indicates standard error of the mean).
Figure 4B:
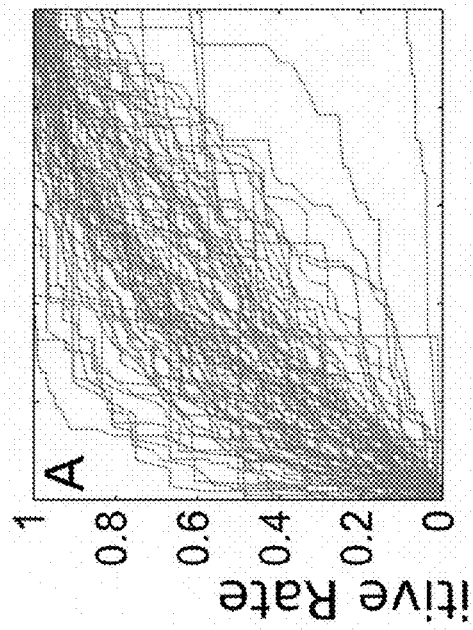
Figure 4C:
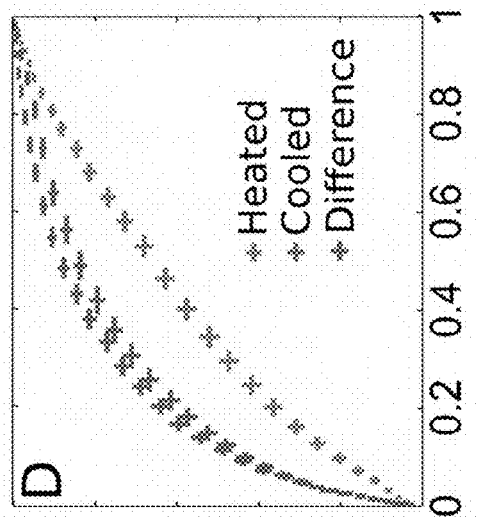
Figure 4D:
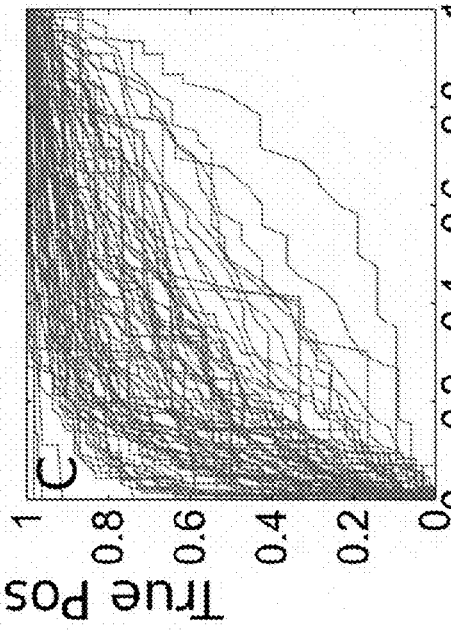

Results:

ROC curves for all n=89 patients are shown in FIGS. 4A-4D. Analyses correlating thermal images and wet/dry encoded visible light images were calculated from thermal images before fan cooling (FIG. 4A), after fan cooling (FIG. 4B), and from the region-by-region difference of pre- and post-cooling thermal images (FIG. 4C). On average, analysis using post-cooling thermal images was more accurate than the other methods, as shown in FIG. 4D, though the method using the difference between pre- and post-cooling thermal images was nearly as accurate. For the post-cooling analysis, the median area under the ROC curve was 0.837

(CI: 0.816 to 0.86), with no clear relationship to age, as shown in FIG. 5A. The median of the best-discriminating temperature was 40.9° C. (1st to 3rd quartile: 40.2° C. to 42.1° C.; FIG. 5B).

Composite analyses of thermal and wet/dry encoded visible light images were compiled to illustrate spatial distributions over the body surface across all patients, as shown in FIGS. 5C-5E. Sweating was most commonly found on the forehead, hands, medial forearms, and to a lesser extent, the upper torso (FIG. 5C), while on average anhidrosis was seen more often along distal (and some proximal) leg areas. The average temperature distribution image shows a corresponding pattern, with cooler measurements recorded in areas that were on average associated with sweating (FIG. 5D). There was a bilateral difference in surface temperatures with hotter temperatures along the right side, possibly due to less effective fan cooling on that side. To address the possibility of an uneven distribution of cooler temperatures as an indication of sweating, the average correlation coefficient over all observed areas was calculated (shown as a positive correlation in FIG. 5E), showing a relatively uniform accuracy across the body surface.

Figures 6A, 6B:
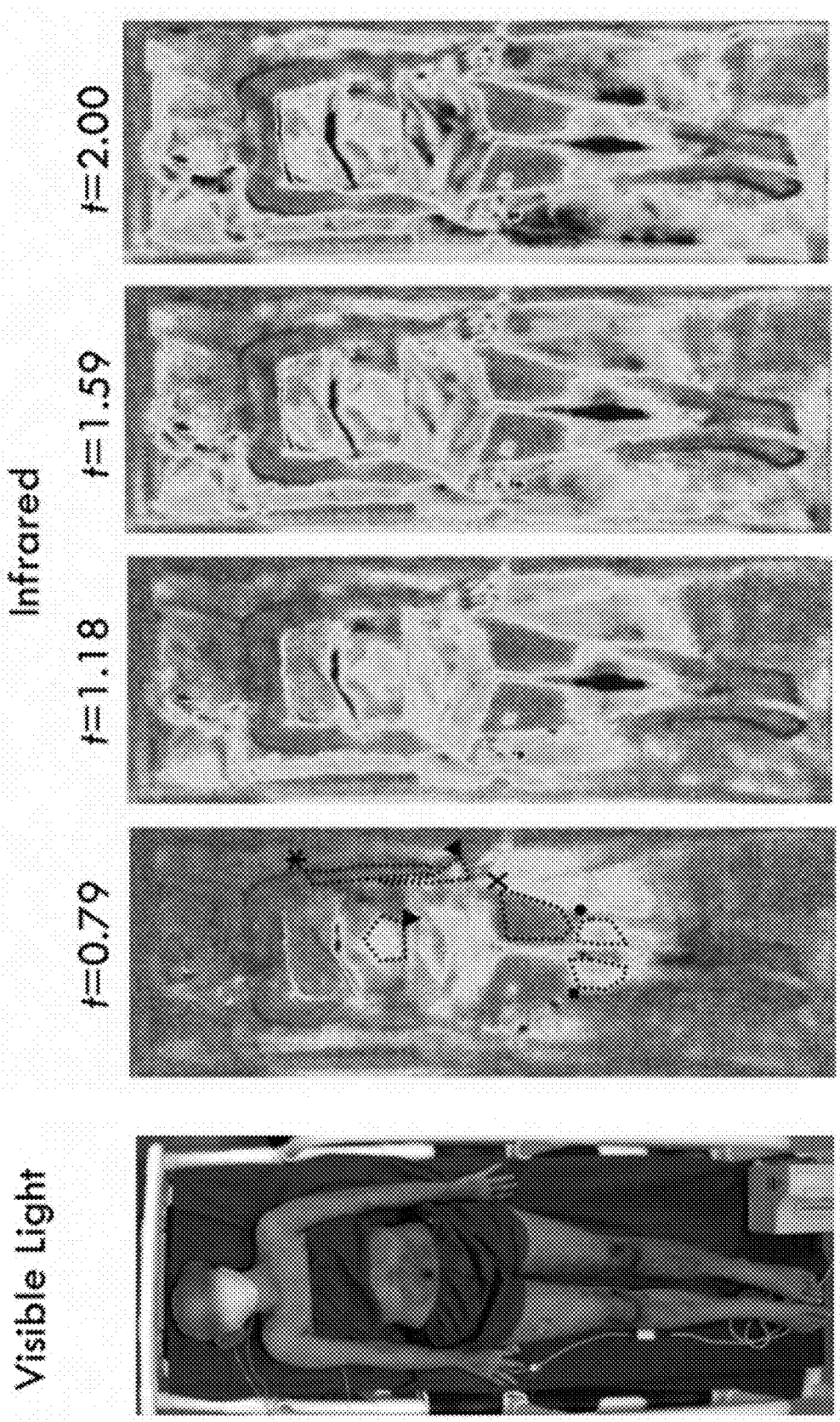
FIGS. 6A-6C show temperature changes with fan cooling during high speed thermal imaging in a representative patient according to embodiments of the invention. Visible light image (FIG. 6A) and sequential infrared difference images during fan cooling (FIG. 6B) with six anatomic regions of interest (shown for t=0.79 s with markers matched to FIG. 6C). As indicated by purple regions in FIG. 6A, two dry and four sweating regions are shown. Sweating regions show a distinct temperature drop within 1 second of fan cooling (FIG. 6C). Wet regions are the abdomen (∫), left knee (•), right knee (■) and medial left forearm (▲). Dry regions are the left thigh (X) and lateral left arm (*).
Figure 6C:
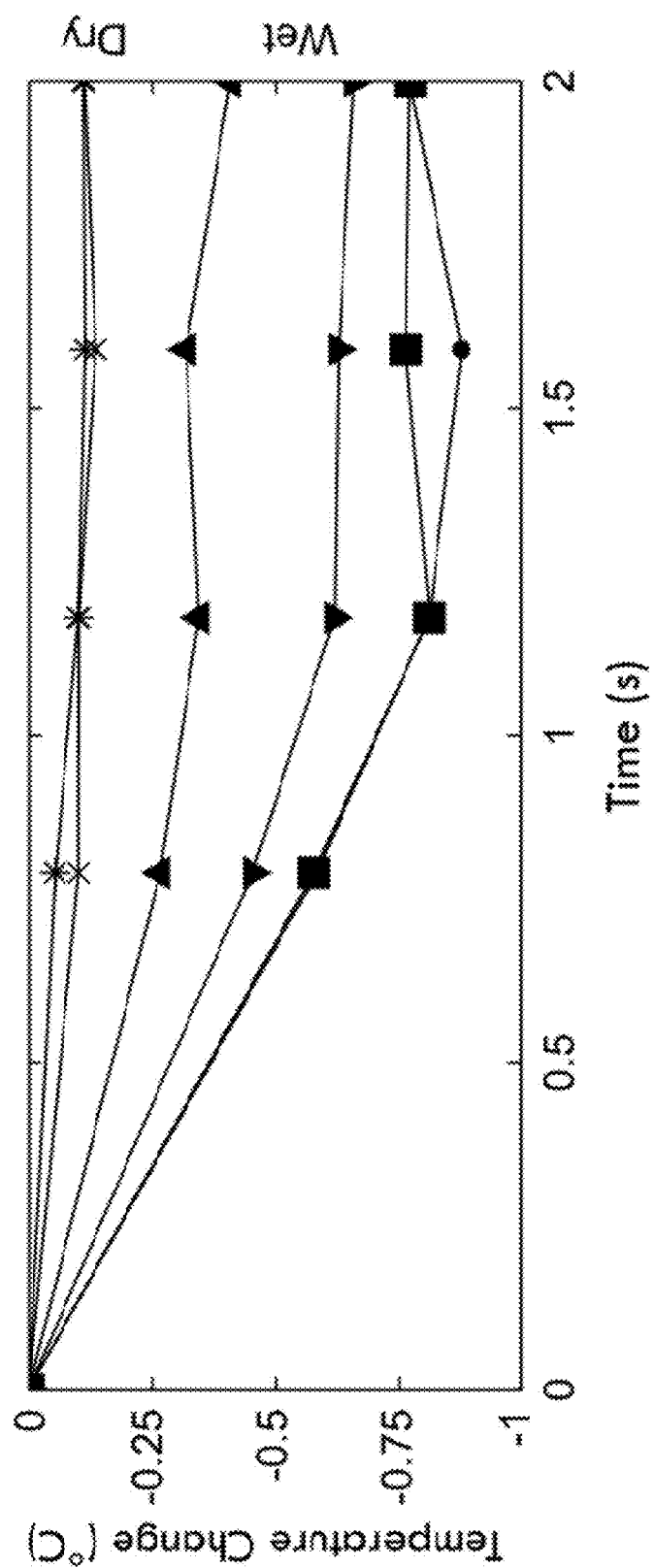

Frame-by-frame analysis of one patient using the image subtraction method, as illustrated in FIGS. 6A-6C, shows that under direct airflow, sweating regions of skin drop approximately 0.5° C. within the first second of cooling, whereas dry regions typically decrease less than 0.25° C., as shown in FIG. 6C.

Discussion:

In contrast to other peripheral nervous system testing modalities, TST provides a means of assessing sudomotor function along the entire neural axis from the central nervous system through peripheral small nerve fibers, which provide sympathetic control over sweat gland function [12]. Q-SWEAT is relatively non-invasive but tests only small areas of the body surface, provides information only about peripheral innervation and the sweat glands, and is not well-suited to testing the most distally innervated portions of the feet and toes [20]. Sympathetic skin responses are not easily graded, tending to be produced in an "all or none" fashion and habituating quickly with repetition [25]. Epidermal nerve fiber density estimation, performed via skin biopsy at multiple sites, can quantify innervation with small fibers. However, this method has not been quantified or normed in children, is invasive when done once and is more invasive with serial measurements [23]. Corneal nerve fiber measurements are less invasive but require special expertise and equipment to obtain the images [6].

TST reveals abnormalities of small sensory and autonomic nerve fiber function which cannot be assessed through standard sensory nerve conduction studies as performed in clinical neurophysiology laboratories. Clinical disorders with neuropathology that can be limited to small nerve fiber dysfunction include complex regional pain syndrome [2] diabetic neuropathy, erythromelalgia [10], multiple system atrophy [21] and autonomic failure [9]. Further, patterns of altered sweating can help identify distal neuropathies and localize pathology to affected spinal nerve roots or peripheral nerves.

TST has been applied successfully in patients as young as two years of age and provided reliable diagnostic data in 98% of 110 children under 16 years of age studied at Mayo Clinic Rochester [17]. However, limitations of the indicator powder method may prevent widespread adoption of this method for use in early diagnosis of neuropathy or other disorders, particularly in pediatrics. Imprecision in the manual application of the powder restricts quantitative analysis. The TST method requires a patient to lie still for up to an hour to keep from disturbing the pattern of the powder. Once testing is finished, the powder can be difficult to completely clean from the skin and can stain clothing if not thoroughly removed [19]. Spatial resolution is good, but local quantitative sweat measurement is not possible. Though reactions to the powder are rare, an abundance of caution requires avoiding ingestion, inhalation or contact with the eyes, meaning that facial sweating is difficult to assess with this method. Furthermore, the length of heat exposure required may be particularly noxious to patients with disorders such as complex regional pain syndrome who may nonetheless benefit from objective and quantitative appraisal. Cumulatively, these difficulties limit the use of this cumbersome, somewhat uncomfortable, technique in younger and less cooperative patients.

The current standard TST reporting method requires a tedious manual and interpretive process to represent regions of color change on a patient photograph as a distribution of pixels on a normalized digital image representing a schematic body shape. This allows quantification of anhidrosis as a ratio of the number of pixels encoded as dry to those composing the whole body schematic. While the calculation of this ratio itself is quantitative, the encoding process requires continuous series of subjective evaluations.

Our semi-automated method, on the other hand, minimizes the interpretive input of the technologist by requiring only the identification of a few exemplar regions representing the most unambiguously wet or dry areas. Thus, this method of encoding images using the traditional indicator powder could make the localization of sweating body surface regions more accurate and objective, with less dependence on individual interpretation. This method has been used successfully in our clinical practice for several years to illustrate patterns of sweating and calculate a global measure of anhidrosis. While this approach constitutes an important incremental improvement in current practice, it does not alleviate many of the intrinsic difficulties of the indicator powder method that prevent its wider adoption.

A more fundamental improvement in current practice, using an infrared camera system, could eliminate the need for the indicator powder altogether. In this study, we have shown that body surface temperature changes produced by forced evaporative cooling correspond closely to regions identified as sweating using the indicator powder. The infrared imaging method produces adequate spatial resolution for clinical purposes and may confer several distinct advantages over the current method using indicator powder. First, thermal imaging eliminates the variability inherent in application of the indicator powder, allowing a potentially more quantitative assessment of local sweating. The sensitivity of this imaging modality may also allow for faster, less burdensome testing by measuring evaporative temperature loss from small volumes of sweat. In addition, though not specifically addressed in this study, thermal imaging may offer a method to simultaneously test sudomotor and vasomotor function within the same protocol. While the application of thermography here is novel in that it measures sweat patterns from forced evaporative heat loss, infrared imaging has been described for some time as a tool for characterizing vasomotor or sudomotor function in healthy human physiology [7], both at rest and in thermodynamically stressed conditions [1, 3-5, 8, 11, 14, 16, 18, 24, 26, 27].

Because this study was a retrospective analysis of data incidental to clinical practice, several limitations should be considered. First, the sampled population may not be representative of that seen in other contexts, nor did we have an opportunity to test our method with a population of healthy controls. Nonetheless, while the underlying neuropathologies (or lack thereof) may differ in other settings, we consider it unlikely that the chemical and physical mechanisms that relate skin surface sweat to indicator powder color change, or to evaporative cooling, would differ depending on these underlying conditions. Still, it is possible (indeed likely) that the evaporative cooling method presented here may be differentially sensitive to sweat volume in ways which may render it more or less applicable to different disorders. Another potential limitation of our use of an existing clinical protocol is that it was not designed to test the limits of infrared imaging in detecting skin surface sweating. However, a close analysis of a representative example infrared video shows that with fast air flow, the temperature difference between sweating and non-sweating regions appears within 1 second of fan cooling. This suggests that, with an optimized cooling and imaging system, sweat patterns could be characterized very quickly, at least in older patients who could follow instructions to hold still. This imaging modality may also be more sensitive than the current method for small amounts of sweat, allowing for a shorter testing protocol overall. While encouraging, the correlations shown here between fan cooling and indicator powder sweat-coded imaging were not perfect. In several patients, region-by-region classification of cooling as characterized by the area under the ROC curve was smaller than would be expected by chance. These cases tended to be those in which there was either a complete absence of sweating or copious global sweating, indicating that the classification algorithm may need to be adjusted to perform more accurately in these extreme cases. Another source of error seemed to be in encodings of regions that had once sweat and subsequently dried during testing. While these regions show a light shade of purple with the indicator powder testing, they may be missed by the infrared evaporative cooling method. It is likely that a more consistent and refined protocol would prove faster, more sensitive and more accurate than the approach described here. For example, instead of a hand-held fan, relay control ceiling fans could produce a more homogeneous and reproducible cooling effect. It is also possible that a method using intermittent heating and fan cooling could identify regions of transitory sweating that are captured by the indicator powder method, but presumably missed by the single cooling cycle approach we used in this study.

In sum, faster, more objective, more quantitative and less cumbersome measurement of sudomotor function could pave the way for more widespread use of these tests, improving detection, assessment and treatment for a number of neurologic disorders affecting sudomotor and/or small nerve fiber function. Ultimately, additional research will be needed to validate the infrared evaporative cooling method and allow for a transition of TST to a completely powderless process to improve patient tolerance and drive more widespread adoption. Until then our results suggest that the current protocol could be made more reproducible and objective with the use of a standard statistical technique.

Example 2

Infrared Imaging of Evaporative Cooling as a Replacement for Indicator Dye Powder in the Identification of Neurological Disorders The objectives of these exemplary studies are, among other things, to replicate previous work establishing that infrared imaging with evaporative cooling (stainless thermoregulatory testing; SST) could identify regions of sweating/non-sweating that well correlated with regions identified with the established method that uses indicator dye powder and visible light imaging; and to replicate these results in tests in which the indicator dye is not used, and to establish that infrared imaging with evaporative cooling alone could identify neuropathy as well as the standard method. For these studies, patients of the neurology service who had done thermoregulatory sweat testing (as part of clinical care, using the standard method) were recruited for repeat studies using the infrared method alone. In addition, several presumptively healthy participants were recruited to be tested using both methods.

Each participant therefore was tested twice: once with indicator powder as well as infrared imaging of evaporative cooling; and once with no powder and only infrared imaging with cooling. The tests using the two methods were performed within a few weeks of each other under the assumption that underlying sweat function would not change over that interval. The hypothesis was that the infrared method with no powder would reproduce the results of the powder test by showing a similar pattern and distribution over the body surface.

Preliminary analysis suggests that the semi-automated pixel coding method (Exemplar-based sweat localization; EOSL) continues to perform well in these replications. The dye coloration pattern, as shown in FIGS. 7A, 8A, 9A, 10A, 11A, and 12A, was reproduced well in the encoded images, as shown in FIGS. 7B, 8B, 9B, 10B, 11B, and 12B. Further, FIGS. 7C, 8C, 9C, 10C, 11C, and 12C also show infrared imaging of evaporative cooling (STT) often produced a similar distribution pattern as the standard dye method. Results for the evaporative cooling method alone were more ambiguous, as shown in FIGS. 7D, 8D, 9D, 10D, 11D, and 12D. In some cases, this modality reproduced the overall pattern of the other method, but there was some question whether the clinical diagnoses could be reliably reproduced from these images. One difference between the two methods that seems to be important is that the in the powder method skin regions that sweat and subsequently dry during the heating phase of the test nonetheless are identifiable from a purple coloration. In infrared imaging of evaporative cooling, on the other hand, if a skin region has once sweat and subsequently dried at the time of fanning, there will be no local cooling in that region, so sweating will not be indicated.

Figures 7A, 7B, 7C, 7D:
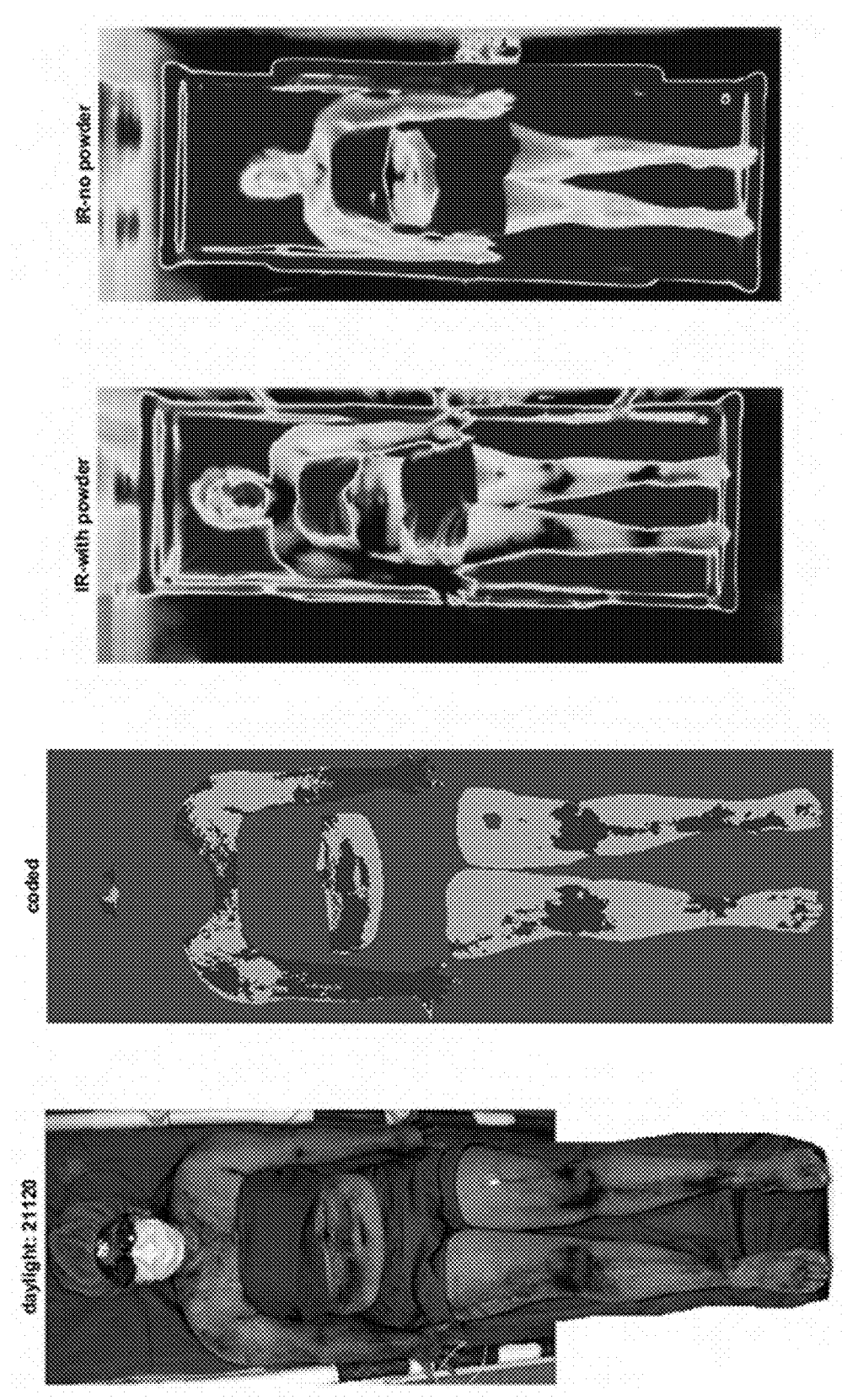
FIGS. 7A-7D show performance and reproducibility of infrared imaging of evaporative cooling as a substitute for color change powder according to embodiments of the invention.

As shown in FIGS. 7A-7C, the simultaneous IR imaging (FIG. 7C) reproduces the pattern seen in the indicator dye imagine (FIG. 7A) and the encoded pattern (FIG. 7B) derived from the indicator dye imagine. The infrared/cooling method alone reproduces some of the same localization, but suggests that re-dried regions are not cooling. Imaging these regions with this method requires more frequent intermittent cooling/imaging.

Referring to FIGS. 8A-8D, the overall pattern is well-reproduced in the simultaneous infrared imaging/cooling (FIGS. 8A-8C), with someone decreased cooling in the repeat study (FIG. 8D). It is unclear whether this difference represents intraindividual variability or a difference in heat exchange from the skin surface due to the absence of the indicator powder itself.

Figures 9A, 9B, 9C, 9D:
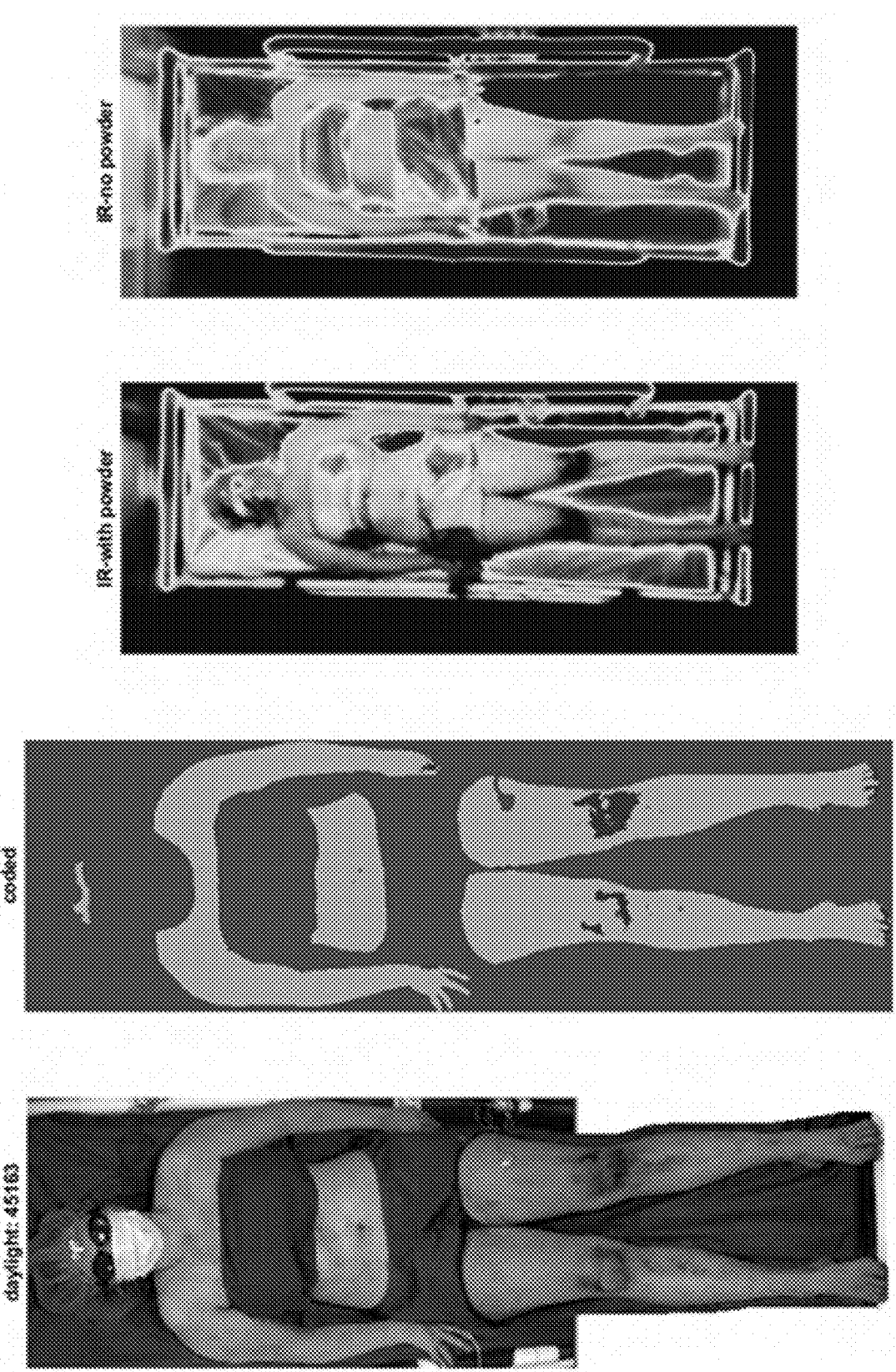
FIGS. 9A-9D show performance and reproducibility of infrared imaging of evaporative cooling as a substitute for color change powder according to embodiments of the invention.

As shown in FIG. 9C, the overall pattern is reproduced well, aside from some excess cooling on the right side of the body, due to the location of the fan used for cooling. This suggests the need for a more controlled laminar flow coming from above the patient.

Figure 10D:
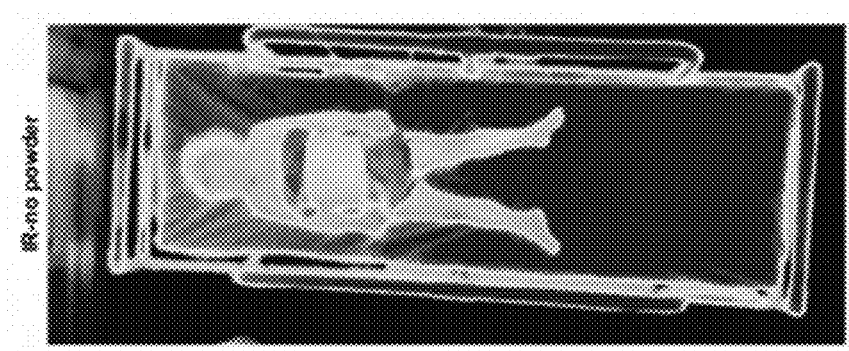
FIGS. 10A-10D show performance and reproducibility of infrared imaging of evaporative cooling as a substitute for color change powder according to embodiments of the invention.
Figure 10C:
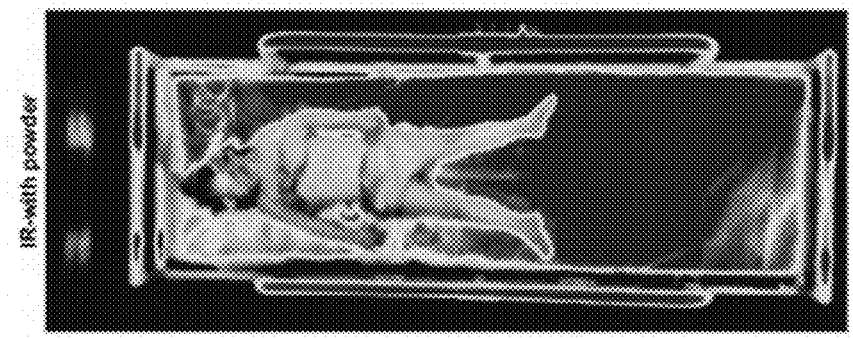
Figure 10B:
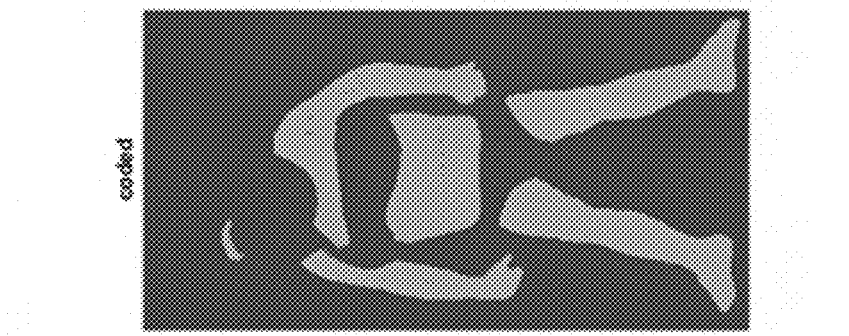
Figure 10A:

As shown in FIG. 10D, without powder, cooling is very limited in a patient with no sweating at all.

Figures 11A, 11B, 11C, 11D:
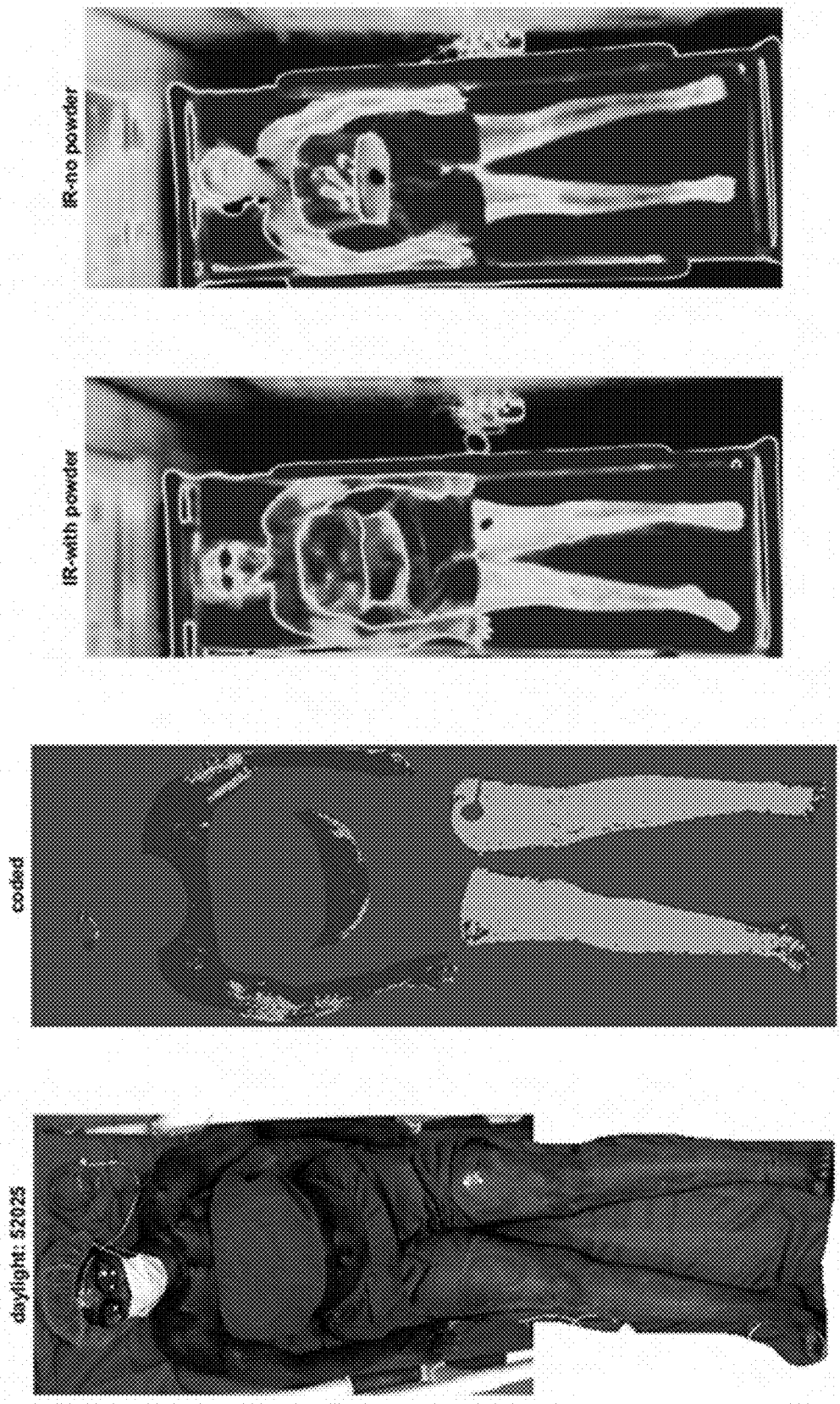
FIGS. 11A-11D show performance and reproducibility of infrared imaging of evaporative cooling as a substitute for color change powder according to embodiments of the invention.

As shown in FIGS. 11B and 11D, results with dark skin tones are similar to those with lighter tones (where indicator dye coloration may be more ambiguous). The infrared only test (FIG. 11D) reproduces most of the spatial distribution of the standard protocol (FIG. 11B), with some loss of cooling in the arms from what appears to be re-drying.

Figures 12A, 12B, 12C, 12D:
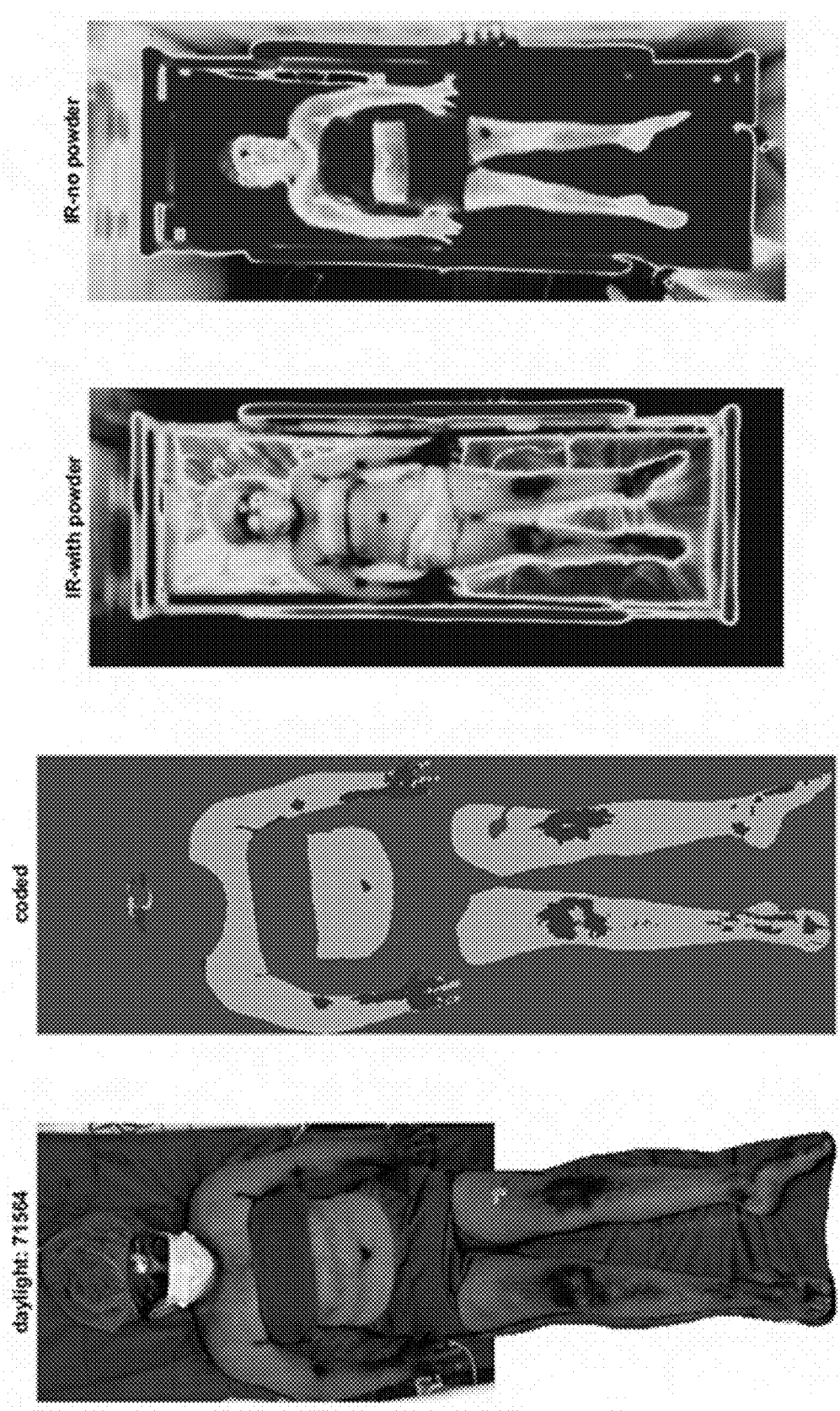
FIGS. 12A-12D show performance and reproducibility of infrared imaging of evaporative cooling as a substitute for color change powder according to embodiments of the invention.

As shown in FIGS. 12C and 12D, the basic pattern is reproduced (cooling in hands, knees, feet and round the neck.

EOSL continued to perform well as a more repeatable and objective method for analyzing sweat distribution from thermoregulatory testing using the indicator dye powder that has been the standard for decades. The more revolutionary technique, stainless thermoregulatory testing (STT), which uses forced evaporative cooling under infrared imaging allows evaluation of sweat patterns without the cumbersome and off-putting indicator dye.

Results of the studies shown here suggest several modifications to the STT protocol (originally developed in the context of the standard clinical protocol). First, evaporative cooling should be provided not by a hand-held consumer fan, but by an array of small fans suspended above the subject such that they provide a uniform, even laminar flow over the body surface. Second, instead of a sustained period of heating to produce a specified core temperature after which imaging is done (as in the standard method), with STT intermittent phases of heating and fan cooling should be used to quickly identify transiently sweating regions. Not only will this alleviate the problem of areas that sweat then dry before imaging, but will allow a more dynamic spatial temporal characterization of the sweat patterns in each subject, perhaps improve discrimination and diagnosis of subtle neurological pathologies or progression of symptoms. It may even be possible to use continuous airflow-based cooling, heating and imaging at the same time to provide a continuous assessment of sweating over the skin surface.

The foregoing description of the exemplary embodiments of the invention has been presented only for the purposes of illustration and description and is not intended to be exhaustive or to limit the invention to the precise forms disclosed. Many modifications and variations are possible in light of the above teaching.

The embodiments were chosen and described in order to explain the principles of the invention and their practical application so as to enable others skilled in the art to utilize the invention and various embodiments and with various modifications as are suited to the particular use contemplated. Alternative embodiments will become apparent to those skilled in the art to which the present invention pertains without departing from its spirit and scope. Accordingly, the scope of the present invention is defined by the appended claims rather than the foregoing description and the exemplary embodiments described therein.

LIST OF REFERENCES

[1]. Barnes R B. Diagnostic thermography. *Appl Opt* 7: 1673-1685, 1968.

[2]. Birklein F, Riedl B, Claus D, and Neundorfer B. Pattern of autonomic dysfunction in time course of complex regional pain syndrome. *Clin Auton Res* 8: 79-85, 1998.

[3]. Birklein F, Sittl R, Spitzer A, Claus D, Neundorfer B, and Handwerker H O. Sudomotor function in sympathetic reflex dystrophy. *Pain* 69: 49-54, 1997.

[4]. Bouzida N, Bendada A, and Maldague X P. Visualization of body thermoregulation by infrared imaging. *Journal of Thermal Biology* 34: 120-126, 2009.

[5]. Brelsford K L, and Uematsu S. Thermographic presentation of cutaneous sensory and vasomotor activity in the injured peripheral nerve. *J Neurosurg* 62: 711-715, 1985.

[6]. Bucher F, Schneider C, Blau T, Cursiefen C, Fink G R, Lehmann H C, and Heindl L M. Small-Fiber Neuropathy Is Associated With Corneal Nerve and Dendritic Cell Alterations: An In Vivo Confocal Microscopy Study. *Cornea* 34: 1114-1119, 2015.

[7]. Clark R P. Human Skin Temperature and Its Relevance in Physiology and Clinical Assessment. In: *Recent Advances in Medical Thermology*, edited by Ring E F J, and Phillips B. Boston, Mass.: Springer New York, 1984, p. 5-15.

[8]. Clark R P, Mullan B J, and Pugh L G. Skin temperature during running—a study using infra-red colour thermography. *J Physiol* 267: 53-62, 1977.

[9]. Cohen J, Low P, Fealey R, Sheps S, and Jiang N S. Somatic and autonomic function in progressive autonomic failure and multiple system atrophy. *Ann Neurol* 22: 692-699, 1987.

[10]. Davis M D, Genebriera J, Sandroni P, and Fealey R D. Thermoregulatory sweat testing in patients with erythromelalgia. *Arch Dermatol* 142: 1583-1588, 2006.

[11]. Deng Z S, and Liu J. Enhancement of thermal diagnostics on tumors underneath the skin by induced evaporation. *Conf Proc IEEE Eng Med Biol Soc* 7: 7525-7528, 2005.

[12]. Fealey R. Thermoregulatory Sweat Test. In: *Clinical Autonomic Disorders: Third Edition*. Baltimore, Md.: Lippincott Williams & Wilkins, 2008, p. 244-260.

[13]. Fealey R. Thermoregulatory Sweat Test. In: *Clinical Autonomic Disorders 2nd ed.* Philadelphia: Lippincott-Raven, 1997, p. 245-257.

[14]. Fushimi H, Inoue T, Nishikawa M, Matsuyama Y, and Kitagawa J. A new index of autonomic neuropathy in diabetes mellitus: heat stimulated thermographic patterns. *Diabetes Res Clin Pract* 1: 103107, 1985.

[15]. Guttmann L. The management of the quinizarin sweat test (Q.S.T.). *Postgrad Med J* 23: 353-366, 1947.

[16]. Huygen F J, Niehof S, Klein J, and Zijlstra F J. Computer-assisted skin videothermography is a highly sensitive quality tool in the diagnosis and monitoring of complex regional pain syndrome type I. *Eur J Appl Physiol* 91: 516-524, 2004.

[17]. Kuntz N L, Hemenway K L, and Fealey R D. Utility of diagnostic thermoregulatory sweat test in children. In: Neurology Lippincott Williams & Wilkins 530 Walnut St, Philadelphia, Pa. 19106-3621 USA, 2011, p. A575-A575.

[18]. Lahiri B B, Bagavathiappan S, Jayakumar T, and Philip J. Medical applications of infrared thermography: A review. *Infrared Physics & Technology* 55: 221-235, 2012.

[19]. Low P A. Testing the autonomic nervous system. *Semin Neurol* 23: 407-421, 2003.

[20]. Low P A, Caskey P E, Tuck R R, Fealey R D, and Dyck P J. Quantitative sudomotor axon reflex test in normal and neuropathic subjects. *Ann Neurol* 14: 573-580, 1983.

[21]. Low P A, Tomalia V A, and Park K J. Autonomic function tests: some clinical applications. *Journal of clinical neurology (Seoul, Korea)* 9: 1-8, 2013.

[22]. Low P A, Walsh J C, Huang C Y, and McLeod J G. The sympathetic nervous system in diabetic neuropathy. A clinical and pathological study. *Brain* 98: 341-356, 1975.

[23]. Provitera V, Gibbons C H, Wendelschafer-Crabb G, Donadio V, Vitale D F, Stancanelli A, Caporaso G, Liguori R, Wang N, Santoro L, Kennedy W R, and Nolano M. A multi-center, multinational age- and gender-adjusted normative dataset for immunofluorescent intraepidermal nerve fiber density at the distal leg. *Eur J Neurol* 23: 333-338, 2016.

[24]. Saxena A K, and Willital G H. Infrared thermography: experience from a decade of pediatric imaging. *Eur J Pediatr* 167: 757-764, 2008.

[25]. Shahani B T, Halperin J J, Boulu P, and Cohen J. Sympathetic skin response—a method of assessing unmyelinated axon dysfunction in peripheral neuropathies. *J Neurol Neurosurg Psychiatry* 47: 536-542, 1984.

[26]. Sun P C, Lin H D, Jao S H, Chan R C, Kao M J, and Cheng C K. Thermoregulatory sudomotor dysfunction and diabetic neuropathy develop in parallel in at-risk feet. *Diabet Med* 25:413-418, 2008.

[27]. Torii M, Yamasaki M, Sasaki T, and Nakayama H. Fall in skin temperature of exercising man. *Br J Sports Med* 26: 29-32, 1992.

What is claimed is:

1. A system for thermoregulatory sweat testing of a living subject having a core body temperature, comprising:
    a chamber for accommodating the living subject, wherein the chamber comprises a heating device for operably elevating the core body temperature of the living subject to a target temperature so as to induce sweating over a skin surface of the living subject;
    a cooling device for operably creating forced evaporative cooling of the skin surface of the living subject after the core body temperature of the living subject is elevated to the target temperature;
    an imaging device for acquiring images of the living subject at different times, each image having imaged pixels, wherein the imaging device comprises one or more infrared cameras, one or more infrared sensors, or a combination of them; and
    a controller coupled with the chamber and the imaging device for controlling operations of the chamber and the imaging device and processing the acquired images to determine skin surface sweat distributions of the living subject,
    wherein the acquired images include:
        one or more images that are acquired after the evaporative cooling is applied to the skin surface of the living subject; and
        a base image that is acquired when the core body temperature of the living subject is elevated to the target temperature and no forced evaporative cooling of the skin surface of the living subject is created,
    wherein the skin surface sweat distributions of the living subject is determined by subtracting pixel color values of the one or more images from that of the base image.

2. The system of claim 1, wherein the heating device comprises infrared heat lamps.

3. The system of claim 1, further comprising at least one probe coupled with the chamber and the controller for operably monitoring a rate of temperature increase and/or ambient heat in the chamber and oral core temperature and/or skin temperature of the living subject, such that when a failsafe mechanism in the chamber, or the oral core temperature or the skin temperature raised beyond a safety threshold values occur, the heating device is turned off.

4. The system of claim 1, further comprising a display for displaying the surface sweat distributions of the living subject.

5. The system of claim 1, wherein the cooling device comprises one or more fans.

6. The system of claim 3, wherein the at least one probe is configured to further monitor humidity in the chamber.

7. A method for thermoregulatory sweat testing of a living subject having a core body temperature, comprising:
    applying a color-change dye to the living subject;
    acquiring a first image of the living subject having imaged pixels;
    elevating the core body temperature of the living subject to a target temperature;
    acquiring a second image of the living subject having imaged pixels;
    specifying a linear discriminant classifier based on pixel color values from the first and second images;
    classifying the imaged pixels as either sweating or non-sweating;
    counting the number of sweating and non-sweating imaged pixels; and
    determining a percentage of non-sweating pixels.

8. The method of claim 7, wherein said specifying the linear discriminant classifier is performed using regions of interest defined within the first and second images, wherein the regions of interest comprises:
    a body region outlining a body of the living subject in the first and second images;
    covered regions outlining unobserved areas of the body of the living subject in the first and second images;
    exemplary dry regions outlining non-sweating areas in the first and second images; and
    exemplary wet areas outlining color-shifts of the color-change dye in the second image.

9. The method of claim 8, wherein said classifying the imaged pixels comprises using the exemplary dry regions and the exemplary wet areas to train a linear classifier to encode wet and dry regions on a pixel-by-pixel basis within the body region and excluding the covered regions, so as to obtain an encoded image.

10. The method of claim 9, wherein said counting the number of sweating and non-sweating imaged pixels comprises counting the number of wet pixels of the wet regions and the number of dry pixels of the dry regions, respectively, in the encoded image.

11. The method of claim 10, wherein the percentage of non-sweating pixels is calculated by dividing the number of dry pixels by the combined total number of wet and dry pixels in the encoded image.

12. A method for thermoregulatory sweat testing of a living subject having a core body temperature, comprising:
    elevating the core body temperature of the living subject to a target temperature;
    acquiring a base infrared image of the living subject having imaged pixels;
    creating forced evaporative cooling of a skin surface of the living subject; and
    acquiring one or more infrared images of the living subject at different times, each image having imaged pixels; and
    determining skin surface sweat distributions of the living subject based on the one or more infrared images, wherein cooling areas in the one or more infrared images are corresponding to sweating areas of the living subject,
    wherein said determining the skin surface sweat distributions comprises subtracting pixel color values of the one or more infrared images from that of the base infrared image.

13. The method of claim 12, wherein the skin surface sweat distributions are dynamic spatial temporal characterization of sweat patterns of the living subject.

14. A non-transitory tangible computer-readable medium storing instructions which, when executed by one or more processors, cause a system to perform a method for thermoregulatory sweat testing of a living subject having a core body temperature, wherein a skin surface of the living subject is applied with a color-change dye, the method comprising:
acquiring a first image of the living subject having imaged pixels;
elevating the core body temperature of the living subject to a target temperature;
acquiring a second image of the living subject having imaged pixels;
specifying a linear discriminant classifier based on pixel color values from the first and second images;
classifying the imaged pixels as either sweating or non-sweating;
counting the number of sweating and non-sweating imaged pixels; and
determining a percentage of non-sweating pixels.

15. The non-transitory tangible computer-readable medium of claim 14, wherein said specifying the linear discriminant classifier is performed using regions of interest defined within the first and second images, wherein the regions of interest comprises:
a body region outlining a body of the living subject in the first and second images;
covered regions outlining unobserved areas of the body of the living subject in the first and second images;
exemplary dry regions outlining non-sweating areas in the first and second images; and
exemplary wet areas outlining color-shifts of the color-change dye in the second image.

16. The non-transitory tangible computer-readable medium of claim 15, wherein said classifying the imaged pixels comprises using the exemplary dry regions and the exemplary wet areas to train a linear classifier to encode wet and dry regions on a pixel-by-pixel basis within the body region and excluding the covered regions, so as to obtain an encoded image.

17. The non-transitory tangible computer-readable medium of claim 16, wherein said counting the number of sweating and non-sweating imaged pixels comprises counting the number of wet pixels of the wet regions and the number of dry pixels of the dry regions, respectively, in the encoded image.

18. The non-transitory tangible computer-readable medium of claim 17, wherein the percentage of non-sweating pixels is calculated by dividing the number of dry pixels by the combined total number of wet and dry pixels in the encoded image.

19. A non-transitory tangible computer-readable medium storing instructions which, when executed by one or more processors, cause a system to perform a method for thermoregulatory sweat testing of a living subject having a core body temperature, the method comprising:
elevating the core body temperature of the living subject to a target temperature;
acquiring a base infrared image of the living subject having imaged pixels;
creating forced evaporative cooling of a skin surface of the living subject; and
acquiring one or more infrared images of the living subject at different times, each image having imaged pixels; and
determining skin surface sweat distributions of the living subject based on the one or more infrared images, wherein cooling areas in the one or more infrared images are corresponding to sweating areas of the living subject,
wherein said determining the skin surface sweat distributions comprises subtracting pixel color values of the one or more infrared images from that of the base infrared image.

\* \* \* \* \*